US012062169B2

(12) United States Patent
He et al.

(10) Patent No.: US 12,062,169 B2
(45) Date of Patent: Aug. 13, 2024

(54) MULTI-FUNCTIONAL COMPUTER-AIDED GASTROSCOPY SYSTEM OPTIMIZED WITH INTEGRATED AI SOLUTIONS AND METHOD

(71) Applicant: Hong Kong Applied Science and Technology Research Institute Company Limited, Hong Kong (CN)

(72) Inventors: Xuejian He, Hong Kong (CN); Lu Wang, Hong Kong (CN); Ping Shun Leung, Hong Kong (CN)

(73) Assignee: HONG KONG APPLIED SCIENCE AND TECHNOLOGY RESEARCH INSTITUTE COMPANY LIMITED, Hong Kong (CN)

( * ) Notice: Subject to any disclaimer, the term of this patent is extended or adjusted under 35 U.S.C. 154(b) by 367 days.

(21) Appl. No.: 17/660,422

(22) Filed: Apr. 25, 2022

(65) Prior Publication Data

US 2023/0342912 A1 Oct. 26, 2023

(51) Int. Cl.
*G16H 50/20* (2018.01)
*A61B 1/00* (2006.01)
(Continued)

(52) U.S. Cl.
CPC ...... *G06T 7/0012* (2013.01); *A61B 1/000096* (2022.02); *A61B 1/2736* (2013.01);
(Continued)

(58) Field of Classification Search
CPC ..................... G06T 7/0012; G06T 1/20; G06T 2207/20081; G06T 2207/20084;
(Continued)

(56) References Cited

U.S. PATENT DOCUMENTS 9,589,374 B1 3/2017 Gao et al.
10,482,313 B2 11/2019 Murthy et al.
(Continued)

FOREIGN PATENT DOCUMENTS

CN 109003659 A 12/2018
CN 109523532 A 3/2019
(Continued)

OTHER PUBLICATIONS

K. Watanabe, et al., Accuracy of endoscopic diagnosis of Helicobacter pylori infection according to level of endoscopic experience and the effect of training, BMC Gastroenterol, Aug. 15, 2013, pp. 1-7, vol. 13: 128, BioMed Central Ltd.
(Continued)

*Primary Examiner* — Cindy Trandai
(74) *Attorney, Agent, or Firm* — EAGLE IP LIMITED

(57) ABSTRACT

A multi-functional, computer-aided gastroscopy system optimized with integrated AI solutions is disclosed. The system makes use of multiple deep-learning neural models to achieve low latency and high-performance requirements for multiple tasks. The optimization is made at three levels: architectural, modular and functional level. At architectural level, the models are designed in such a way that it is able to accomplish HP infection classification and detection of some lesions for one inference in order to reduce computation costs. At modular level, as a sub-model of HP infection classification, the site recognition model is optimized with temporal information. It not only improves the performance of HP infection classification, but also plays important roles for lesion detection and procedure status determination. At functional level, the inference latency is minimized by configuration and resource aware optimization. Also at functional level, the preprocessing is speeded up by image resizing parallelization and unified preprocessing.

20 Claims, 19 Drawing Sheets

(51) Int. Cl.

| | |
|---|---|
| ***A61B 1/273*** | (2006.01) |
| ***G06T 1/20*** | (2006.01) |
| ***G06T 7/00*** | (2017.01) |
| ***G06V 10/40*** | (2022.01) |

(52) U.S. Cl.
CPC ................ *G06T 1/20* (2013.01); *G06V 10/40* (2022.01); *G06T 2207/20081* (2013.01); *G06T 2207/20084* (2013.01); *G06T 2207/30092* (2013.01); *G06T 2207/30096* (2013.01)

(58) Field of Classification Search
CPC . G06T 2207/30092; G06T 2207/30096; G06T 2207/10016; G06T 2207/10068; G06T 2207/30028; G06T 7/143; G06T 2207/30032; A61B 1/000096; A61B 1/2736; A61B 1/000094; A61B 1/31; A61B 1/00043; A61B 1/0005; A61B 5/0013; A61B 5/42; A61B 5/7267; A61B 5/7275; G06V 10/40; G06V 2201/031; G06V 10/764; G06V 10/82; G16H 50/20; G16H 50/30
See application file for complete search history.

(56) References Cited

U.S. PATENT DOCUMENTS

| | | | | |
|---|---|---|---|---|
| 10,789,462 | B2 | 9/2020 | Bakalo et al. | |
| 10,861,151 | B2 | 12/2020 | Liang et al. | |
| 11,527,323 | B2 * | 12/2022 | Michuda | G16B 30/00 |
| 2017/0256055 | A1 * | 9/2017 | Teramura | G06T 7/0012 |
| 2020/0279368 | A1 | 9/2020 | Tada et al. | |
| 2021/0097331 | A1 * | 4/2021 | Kamon | G06T 7/0012 |
| 2021/0235980 | A1 * | 8/2021 | Oosake | G06N 3/08 |
| 2021/0256701 | A1 * | 8/2021 | Nozaki | G16H 50/30 |
| 2021/0390693 | A1 * | 12/2021 | Zhang | A61B 1/000096 |
| 2022/0020496 | A1 * | 1/2022 | Saito | G06T 7/0012 |
| 2022/0031227 | A1 | 2/2022 | Cho et al. | |
| 2022/0246303 | A1 * | 8/2022 | Sakaguchi | G06F 13/00 |
| 2022/0296081 | A1 * | 9/2022 | Nygaard Espeland | G06F 18/24133 |
| 2022/0369920 | A1 * | 11/2022 | Freedman | G06T 7/0012 |
| 2023/0148855 | A1 * | 5/2023 | Wang | A61B 1/31<br>382/128 |
| 2023/0255467 | A1 * | 8/2023 | Ikenoyama | G16H 30/40<br>382/128 |
| 2023/0260117 | A1 * | 8/2023 | Matsuzaki | G06V 10/82<br>382/128 |
| 2023/0301503 | A1 * | 9/2023 | Kim | A61B 1/000096 |
| 2023/0353879 | A1 * | 11/2023 | Nishide | A61B 1/0684 |
| 2024/0127433 | A1 * | 4/2024 | Du | G16H 50/20 |

FOREIGN PATENT DOCUMENTS

| | | | |
|---|---|---|---|
| CN | 110495847 | A | 11/2019 |
| CN | 106233719 | B | 3/2020 |
| CN | 107256552 | B | 8/2020 |
| CN | 112651375 | A | 4/2021 |
| CN | 112823396 | A | 5/2021 |
| CN | 112971688 | A | 6/2021 |
| CN | 113344927 | A | 9/2021 |
| WO | 2021132633 | A1 | 7/2021 |

OTHER PUBLICATIONS

"BCEWithLogitsLoss", Retrieved from the internet <URL: https://pytorch.org/docs/stable/generated/torch.nn.BCEWithLogitsLoss.html> [retrieved on May 27, 2022].

Francois Chollet, Xception: Deep Learning with Depthwise Separable Convolutions, Proceedings of the IEEE conference on computer vision and pattern recognition, Apr. 4, 2017, pp. 1251-1258.

* cited by examiner

400

| Index | HP Features |
|---|---|
| L0 | Enlarged Fold + Sticky Mucus + Nodularity + Spotty Redness + Diffuse Redness + Swelling |
| L1 | Atrophy + Intestinal Metaplasia |
| L2 | Other HP- (red streak, hematin ...) |
| L3 | Regular arrangement of collecting venules |
| L4 | Map-like redness |
| L5 | Fundic gland polyposis (FGP) |
| L6 | Bile reflux |
| L7 | Lymphangiectasis |
| L8 | Normal |

| **Indexd** | **Site label** |
|---|---|
| **S1** | Esophagus |
| **S2** | Gastroesophageal junction |
| **S3** | Mid-upper body |
| **S4** | Lower body |
| **S5** | Antrum |
| **S6** | Retro Mid-upper body |
| **S7** | Incisura |
| **S8** | Fundus |
| **S9** | Duodenum |
| **S10** | Descending duodenum |
| **S11** | Larynx |
| **S12** | Others |

Fig. 6

Example of model selection

| GPU Index | | 0 | | | | | 1 | | | | |
|---|---|---|---|---|---|---|---|---|---|---|---|
| Model ID | | 1 | 2.1 | 2.2 | 3.1 | 3.2 | 1 | 2.1 | 2.2 | 3.1 | 3.2 |
| Availability level of computation Resoures | 2001 | | Y | | Y | | Y | | Y | | Y |
| | 2002 | Y | | | | Y | | Y | Y | Y | |
| | 2003 | | Y | Y | Y | | Y | | | | Y |
| | 2004 | Y | Y | Y | | | | | | Y | Y |

Note: Shaded stands for high level of computation resources

Fig. 20

MULTI-FUNCTIONAL COMPUTER-AIDED GASTROSCOPY SYSTEM OPTIMIZED WITH INTEGRATED AI SOLUTIONS AND METHOD

FIELD OF INVENTION

This invention generally relates to a computer-aided gastroscopy system, and in particular to a multi-functional, computer-aided gastroscopy system optimized with integrated AI solutions thereof.

BACKGROUND OF INVENTION

Deep learning-based technology was recently reported to be highly beneficial in the field of endoscopy. According to some of the trials, detection rate could be improved by roughly 50% while endoscopy-related cost could be reduced by 7-20%. Although there are several commercial products with AI functions emerging in the endoscopy industry, many of them still have various kinds of limitations and there are still many challenges in developing a versatile gastroscopy system that can achieve low latency and accurate performance, handle 4K video stream from the latest gastroscopy instrument, detect different lesions, cancers, Helicobacter pylori (HP) infection at the same time, and can run under different hardware configurations. It is therefore an object of this invention to develop a multi-functional, tightly integrated gastroscopy system optimized with AI solutions

SUMMARY OF INVENTION

In the light of the foregoing background, a multi-functional, computer-aided gastroscopy system optimized with integrated AI solutions thereof are provided.

Accordingly, an exemplary embodiment of the present invention provides a computer-aided gastroscopy system comprising: a central processor unit coupled with a memory that stores an executable software program, wherein the software program comprises an AI image processing system that analyzes a gastric image sequence obtained from a gastroscopy instrument. The AI image processing system comprises at least three modules at the architecture level that cooperatively perform image quality assessment, lesion detection and cancer identification, HP classification and site recognition wherein at least one of the modules comprises one or more neural models with each neural model extracting different but related information from the gastric image sequence and sharing the information extracted from the gastric image sequence with other modules; and at least one said neural model fuses HP infection features and site information extracted from other neural models together to boost the classification accuracy of the computer-aided gastroscopy system.

Another exemplary embodiment of the present invention provides a method of processing a gastric image sequence by a computer-aided gastroscopy system comprising: obtaining the gastric image sequence images sequence from a gastroscopy instrument, analyzing the gastric image sequence by an AI image processing system comprising at least three modules at the architecture level that cooperatively performs image quality assessment, lesion detection and cancer identification, HP classification and lesion site recognition wherein at least one of the modules comprises one or more neural models with each neural model extracting different but related information from the gastroscopy image sequence and sharing the information extracted from the gastric image sequence with other modules; and at least one said neural model fuses the HP infection features and site information extracted from other neural network models together to boost the classification accuracy of the computer-aided gastroscopy system, creating a list of subtasks by each of the at least three modules to be executed by the computer-aided gastroscopy system, and reducing the latency response to a user when the computer-aided gastroscopy system further comprises at least one coprocessor and the software program executed at the central processor unit of the computer-aided gastroscopy system judiciously allocates subtasks to the at least one coprocessor depending on a pre-assigned priority of the subtasks and the capacity and capability of each of the coprocessor such that the computer-aided gastroscopy system is able to achieve high detection and classification accuracy with low latency response to the user.

The above example embodiments have benefits and advantages over conventional technology. For example, not only can the disclosed computer-aided gastroscopy system meet all the detection and classification performance criteria set forth by the medical professionals, but it is also able to run on different hardware platforms with various computational capabilities so as to achieve low latency.

BRIEF DESCRIPTION OF FIGURES

Through the following detailed description with reference to the accompanying drawings, the above and other features, advantages and aspects of embodiments of the present invention will become more apparent. In the drawings, identical or similar reference signs represent identical or similar elements, wherein:

FIG. 4 shows a table of HP features for HP classification according to one embodiment of the present disclosure;

FIG. 6 shows the site labels for gastric site recognition according to an embodiment of the present disclosure;

FIG. 20 shows how model selection is done in one exemplary embodiment of the present disclosure.

DETAILED DESCRIPTION

Figure 1:
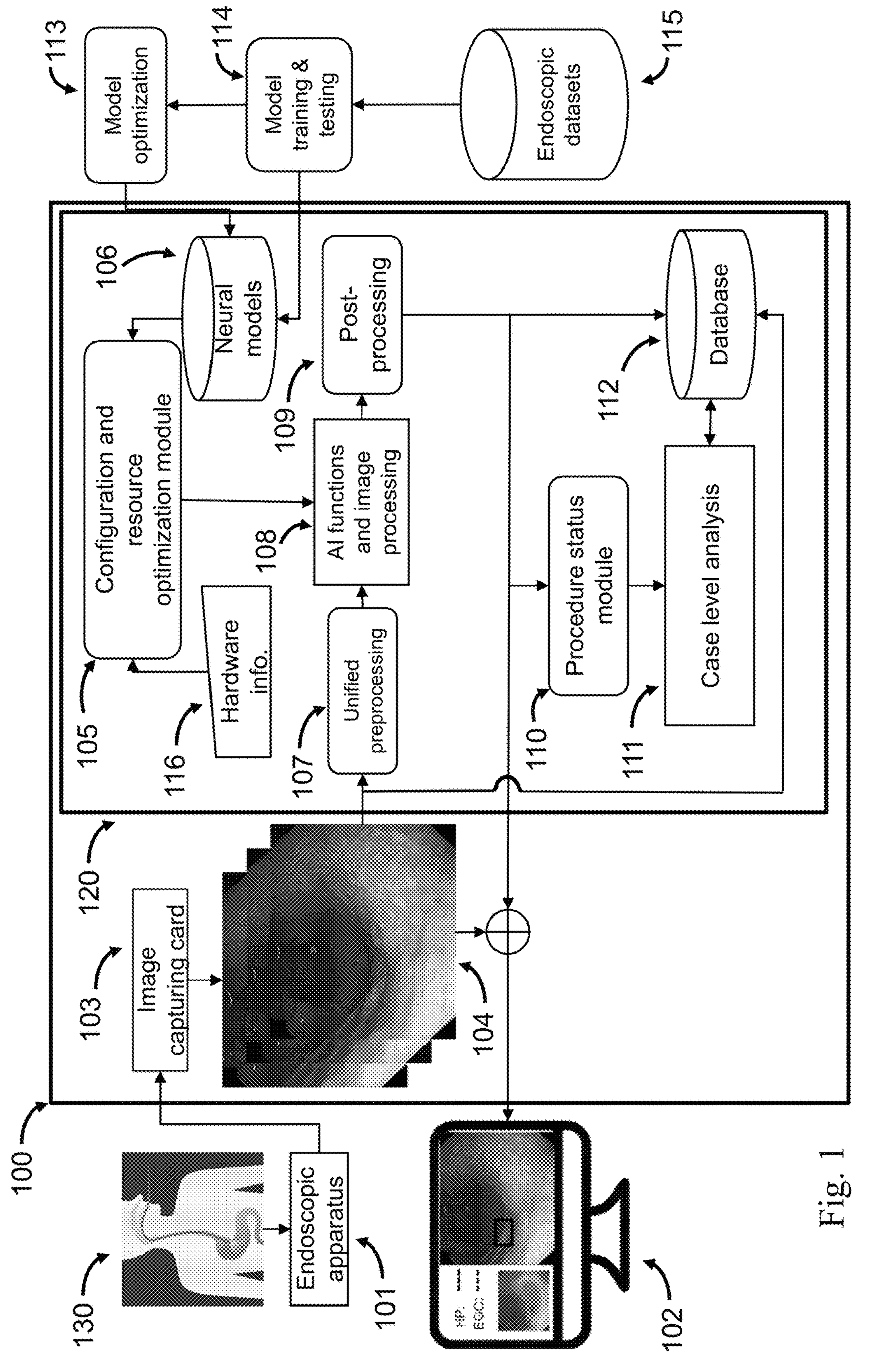
FIG. 1 shows a block diagram of a computer-aided gastroscopy system according to embodiments of the present disclosure.

As used herein and in the claims, "comprising" means including the following elements but not excluding others. The term "based on" is to be read as "based at least in part on." The term "one example embodiment" and "an example embodiment" are to be read as "at least one example embodiment." The term "another embodiment" is to be read as "at least one other embodiment."

As used herein and in the claims, "module" by itself generally refers to a major software component in software unless otherwise specified.

As used herein and in the claims, "neural model" refers to a neural network with a pre-specified neural architecture. "Neural architecture" refers to a particular inter-connection configuration among nodes of different layers of a neural network.

As used herein and in the claims, "tensor" refers to a multi-dimensional mathematical object. As an example, a [256×256×3] tensor denotes a three-dimension array whose first and second dimension is 256 and the third dimension is 3. The last dimension is also referred as "channels" of this tensor.

As used herein and in the claims, "image" refers to a digital image having a plurality of pixels arranged in a two-dimensional array with a certain height and width. "Video" is a sequence of images arranged in certain sequential order. An image within a video is also called a "frame". An image with a label denoting a certain attribute of that image is called a "labelled image" and a "pseudo video" is a collection of labelled images in a certain sequential order to mimic a video. Throughout this specification, the terms "video", and "image sequence" are used interchangeably and both denote an ordered sequence of images.

The present invention presents a computer-aided gastroscopy system. A gastroscopy is a medical procedure that involves inserting a thin, flexible tube called an endoscope through the mouth of a patient to investigate the interior condition of the esophagus, stomach and duodenum. The tip of the flexible tube is equipped with a camera and a light source. The camera captures a video throughout the entire gastroscopy procedure and the video will then be examined by a medical expert or a computer-aided system to check if there is any abnormal growth or lesion inside the gastrointestinal track.

The gastric video may review whether the patient is infected with Helicobacter pylori (HP) virus or there are polys, ulcers or cancer tumors in the stomach. HP infection is the leading cause of HP infection-associated gastritis and, if left unnoticed, may eventually develop into gastric cancers. Hence it is important to diagnose HP infection at the early stage. On top of HP infection, the gastric video may also review other kinds of abnormal growth or lesion inside the stomach. It is therefore advantageous to develop a computer-aided gastroscopy system that can assist medical professionals to analyze the gastric video and report the findings. In recent years, AI techniques based on deep learning technology have been proved successful in various medical image analysis applications. In this invention, deep learning based neural algorithms are developed to assist endoscopists in routine screening of 1-IP infection and other stomach diseases with an aim to improve diagnosis efficiency and accuracy.

There are several challenges in developing such a system. First of all, the system must meet a set of performance criteria specified by the medical community. Such requirements are usually stipulated as a set of performance targets including, but not limited to, disease classification accuracy, detection sensitivity and selectivity, etc. Secondly, it is preferable that the system is able to process the gastric video stream in real-time so that medical professionals can view the results while performing the gastroscopy procedure. Thirdly, the system needs to carry out multiple diagnostic tasks simultaneously on the same video stream, including but not limited to HP infection detection, lesion detection, organ site recognition and tumour classifications. Each of these tasks may call for a dedicated deep learning neural network to analyse the same gastric video. However, these deep learning neural networks are very computationally demanding—both in computational speed and memory requirements. On the other hand, recent endoscope may be equipped with a very high-resolution camera. While this provides better image clarity to the end users, it also demands more computational power to process such images. To this end, the computer-aided system needs to install additional computational hardware or else it is not possible to meet the real-time requirement. Nonetheless, it is desirable that the system can support different computing hardware configurations with different computational capabilities. For low-end configuration, the system may not offer real-time response. But off-line processing may still be useful in some applications. High-end hardware configuration with additional coprocessors can certainly reduce the system response time, but it is costly to deploy. Hence it is a big challenge to develop a system that can provide both low-latency and high performance with minimal additional hardware accelerators.

To overcome all the aforementioned challenges. The computer-aided gastroscopy system is optimized at three levels: architectural, modular and functional level. At the architectural level, the models are designed in such a way that it is able to accomplish HP infection classification and detection of some lesions for one inference in order to reduce computation costs. At the modular level, as a sub-model of HP infection classification, the site recognition model is optimized with temporal information. It not only improves the performance of HP infection classification, but also plays important roles for lesion detection and procedure status determination. At the functional level, the inference latency is minimized by configuration and resource aware optimization. Also at the functional level, the preprocessing is speeded up by image resizing parallelization and unified preprocessing.

Numbered Embodiments

Set 1

1. A computer-aided gastroscopy system, comprising:

a central processor unit coupled with a memory that stores an executable software program, wherein the software program comprises:

an AI image processing system that analyzes a gastric image sequence obtained from a gastroscopy instrument, wherein the AI image processing system comprises at least three modules at the architecture level that cooperatively perform image quality assessment; lesion detection; cancer identification; HP classification; and site recognition, wherein at least one of the modules comprises one or more neural models, the neural model extracting different but related information from the gastric image sequence and sharing the information extracted from the gastric image sequence with other modules; and at least one said neural model fuses HP infection features and site information extracted from other neural models together to boost the classification accuracy of the computer-aided gastroscopy system.

2. The system according to embodiment 1, wherein the at least three modules comprise:

a first module for image quality control to filter out unqualified images in the gastric image sequence;

a second module for lesion detection, cancer identification and lesion tracking; and a third module for classifying HP infection and site recognition, wherein each of these modules comprises one or more neural models.

3. The system according to embodiment 2, wherein the third module further comprises a composite neural model comprising a first neural model taking the gastric image sequence as input, performing HP feature extraction, and outputting a first number of feature channels;

a second neural model also taking the gastric image sequence as input, performing site feature extraction comprising the spatial and temporal site information of the gastrointestinal track, and outputting a second number of feature channels; and a third neural model taking the concatenation of the first number of feature channels and the second number of feature channels as input and producing a third number of class labels, each of the class labels indicating a HP infection feature.

4. The system of embodiment 3, wherein the first neural model products a first tensor of sixty-four channel elements; the second neural model products a second tensor of twelve channel elements, each of the twelve channel elements corresponding to a site classification label; and the third neural model takes the concatenation of the first tensor and the second tensor as input and outputs nine element classification labels corresponding to nine of the HP infection features.

5. The system according to embodiment 3, further comprising a unified preprocessing module wherein the unified preprocessing module takes the gastric image sequence as input and produces a unified tensor as output for each image in the gastric image sequence. The unified tensor is fed to the neural models of the first module, the second module and the third module of the AI image processing system.

6. The system according to embodiment 5, wherein neural network architectures of the first module, the second module and the third module are adjusted such that output tensors of the neural model remain the same as if each of the neural network architectures uses a distinct preprocessing module specially designed for the neural network architecture.

7. The system according to embodiment 5, wherein neural network architectures of the first module, the second module and the third module are adjusted so that the performance of each neural model does not degrade.

8. The system according to embodiment 5, wherein if either the height or the width of the image in the gastric image sequence entering into the unified preprocessing module is higher than a threshold, a parallelized resizing process is invoked to resize the image wherein the parallelized resizing process comprises the following steps:

padding the original image with a row of zeros if the height is an odd number and with a column of zeros if the width is an odd number;

partitioning a padded image into four quadrants;

resizing each of the quadrants in parallel to produce four resized quadrants; and stitching the four resized quadrants together to obtain a uniform resized image.

9. The system according to embodiment 2, wherein the neural model of the first module is trained using an image quality dataset to produce a full image quality neural model;

the one or more neural models of the second module is trained using a lesion dataset to produce a full lesion detection neural model; and the one or more neural models of the third module is trained using a gastric site dataset and a *H. pylori* dataset to produce a full HP-plus-site neural model.

10. The system according to embodiment 9, further comprising a model pruning and quantization module wherein the full image quality neural model, the full lesion detection neural model and the full HP-plus-site neural model are optimized by pruning the layer connections and quantizing the connection weights to produce an optimized image quality neural model; an optimized lesion detection neural model and an optimized HP-plus-site neural model respectively.

11. The system according to embodiment 10, wherein the computer-aided gastroscopy system further comprises at least one coprocessor and the software program executed at the central processor unit judiciously allocates subtasks initiated by each of the modules to the at least one coprocessor depending on a pre-assigned priority of the subtasks and the capability of each of the coprocessor such that the computer-aided gastroscopy system is able to achieve high detection and classification accuracy with low latency response to a user.

12. The system according to embodiment 11, wherein when the computer-aided gastroscopy system is equipped with the at least one coprocessor, the computer-aided gastroscopy system is capable of operating in both off-line processing mode and on-line processing mode.

13. The system according to embodiment 12, wherein when the computer-aided gastroscopy system is set to operate in the off-line processing mode, the computer-aided gastroscopy system configures each of the at least one coprocessor to operate a dynamic batching process which comprises the steps of:

loading at least one full neural model to the coprocessor; and loading a batch of gastric images to the coprocessor wherein the batch size is dynamically determined based on the computation capability and resources available in the coprocessor.

14. The system according to embodiment 12, wherein when the computer-aided gastroscopy system is equipped with the at least one coprocessor and is set to operate in the on-line processing mode, the computer-aided gastroscopy system performs a latency control procedure which comprises the steps of:

pre-determining the loading priority of each of the optimized neural models according to its computational resource requirements;

loading one or more of the optimized neural models to each of the coprocessor according to the loading priority and the hardware configuration of the coprocessor;

establishing a fixed length task queue to each of the coprocessor for the central processing unit to issue subtasks to the task queue for the coprocessor to execute; and enabling each of the at least one coprocessor to operate in parallel wherein whenever the coprocessor becomes idle, the coprocessor deques the subtask from the task queue associated with the coprocessor and starts executing the subtask whenever the coprocessor becomes idle.

15. The system according to embodiment 14, wherein when the computer-aided gastroscopy system obtains the gastric images, the computer-aided gastroscopy system performs a resource-aware inferencing procedure which comprises the steps of:

selecting a coprocessor with the shortest work queue among the at least one coprocessor as a designated coprocessor;

loading one or more of the optimized neural model to the designated coprocessor based on a neural model priority and the resource availability at the designated coprocessor;

repeating the selecting and loading steps such that as many of the optimized neural models are loaded to one or more of the coprocessor as possible;

enabling each of the neural models to start inferencing at each of the at least one coprocessor in parallel performing inter-coprocessor communication among the coprocessors when an inferencing task of the neural model is split to run on more than one of the coprocessors and an intermediate result generated by one of the coprocessors needs to be shared to the other coprocessors; and collecting the inferencing results of each of the neural models and reporting back to the computer-aided gastroscopy system.

16. A method of processing a gastric image sequence by a computer-aided gastroscopy system, comprising:

obtaining the gastric image sequence from a gastroscopy instrument;

analyzing the gastric image sequence by an AI image processing system comprising at least three modules at the architecture level that cooperatively perform image quality assessment; lesion detection; cancer identification; HP classification; and lesion site recognition, wherein at least one of the modules comprises one or more neural models, the neural model extracting different but related information from the gastroscopy image sequence and sharing the information extracted from the gastroscopy image sequence with other modules; and at least one said neural model fuses the HP infection features and site information extracted from other neural network models together to boost the classification accuracy of the computer-aided gastroscopy system;

creating a list of subtasks by each of the at least three modules to be executed by the computer-aided gastroscopy system; and reducing the latency response to a user when the computer-aided gastroscopy system further comprises at least one coprocessor and the software program executed at the central processor unit of the computer-aided gastroscopy system judiciously allocate subtasks to the at least one coprocessor depending on a pre-assigned priority of the subtasks and the capacity and capability of each of the coprocessor such that the computer-aided gastroscopy system is able to achieve high detection and classification accuracy with low latency response to the user.

17. The method of embodiment 16, wherein the analyzing step further comprises the steps of:

filtering out unqualified images in the gastric image sequence by the neural model in a first module;

performing lesion detection, cancer identification and lesion tracking by at least one of the neural models in a second module; and classifying HP infection and recognizing gastrointestinal site by at least one of the neural models in a third module.

18. The method of embodiment 17, wherein the classifying and recognizing step further comprises the steps of:

outputting a first number of feature channels by a first neural model which takes the gastric image sequence as input and performs HP feature extraction;

outputting a second number of feature channels by a second neural model which also takes the gastric image sequence as input and performs site feature extraction comprising spatial and temporal site information of the gastrointestinal track; and producing a third number of class labels by a third neural model which takes the concatenation of the first number of feature channels and the second number of feature channels as input, wherein each of the class labels indicating a HP infection feature.

19. The method of embodiment 18, wherein the second neural model is a composited neural model comprising a site feature extractor model, a LSTM model and a final neural model and the composited neural model is trained according to the following steps:

creating a cumulative batch of gastric images from a full set of labelled gastric images stored in a gastric site dataset;

training an auxiliary neural network using the cumulative batch of gastric images;

copying the entire auxiliary neural network and using the entire auxiliary neural network as a feature extractor of the composited neural model wherein the connection weights of the feature extractor will not be modified during the subsequent training process;

creating a pseudo video using the full set of labelled gastric images and collecting a predefined number of labelled gastric images from the pseudo video to form a batch unit;

grouping a predefined number of batch units together as a batch group and sending the batch group to the feature extractor to produce a feature tensor of the batch group;

feeding the feature tensor to the LSTM model which produces an intermediate tensor;

sending the intermediate tensor to the final neural model comprising at least one fully connected layer wherein the output tensor of the final neural model comprises a site vector, each element in the site vector is a site label and represents a gastric site location and the site vector becomes the feature channels of the second neural model.

20. The method of embodiment 19, wherein the pseudo video is created according to the following steps:

sorting the labelled gastric images in the gastric dataset in ascending order according the index of the site label to obtain a sorted list of gastric images creating a pre-specified number of random generators, each of the random generators generating random numbers within a predetermined random range;

selecting one of the random generators to generate an initial random number and using that initial random number to select a gastric image from the sorted list as an anchored image;

collecting a set of random numbers from each of the plurality of random generators wherein the total number of random numbers collected is a predefined number being the batch size of the batch unit;

converting the set of random numbers into an index list offset by the index of the anchored image; and using the offset index list to select gastric images from the sorted list to form the batch unit.

System Architecture

Referring now to FIG. 1, a computer-aided gastroscopy system 100 is disclosed. The system comprises an image capturing card 103, which captures a sequence of digital images from an endoscopic apparatus 101. In one embodiment, this endoscopic apparatus 101 comprises an image camera and a light source which can be inserted inside an organ inside the human body 130. When this endoscopic apparatus 101 is used to investigate the esophagus and the stomach, it is usually referred to as a gastroscopy instrument.

The image capturing card generates a video sequence of images 104 which is sent to the endoscopic image analysis module 120 for further analysis. In one embodiment, the endoscopic image analysis module 120 comprises a unified preprocessing module 107 that receives the sequence of images 104 and re-sizes each image to a standard size before they are fed to the AI functions and image processing module 108. This module performs the major analysis to detect any abnormalities on the sequence of images 104 and will be discussed in detail later. The results of such analysis are sent to the post-processing module 109. After post-processing, the outcomes are sent to both the database 112, the procedure status module 110 as well as to a monitor 102 where the outcomes are displayed to the end-users together with the sequence of images 104.

In one embodiment, the procedure status module 110 captures all the information of the gastroscopic analysis procedure which includes the patient's information, the start and end of the gastroscopy procedure, as well as the post-processing outcome, and feeds them to the case level analysis module 111 to create a diagnostic case for this patient. This diagnostic case, together with the outcome from the post-processing module 109, and the sequence of images 104 are stored in the database 112.

In one embodiment, the AI functions and image processing module 108 employ one or more neural models 106 to do the image processing and analysis, and they are very computationally intensive. Thus, the endoscopic image analysis module 120 is designed to utilize all the hardware resources available in the system to speed up the response time. In particular, the computer-aided gastroscopy system is developed to run on various hardware platforms, either equipped with or without graphic processing unit (GPU) coprocessor(s). The configuration and resource optimization module 105 takes into consideration of the hardware information 116 and attempts to configure and schedule multiple tasks generated by the neural modules 106 so that the AI functions and image processing module 108 can execute those tasks in parallel in order to speed up the turn-around time.

To this end, the neural models need to be trained before they can classify and detect any abnormalities in the sequence of gastric images. The model training and testing module 114 makes use of the endoscopic datasets 115 to train each neural model so that the entire system performance of the computer-aided gastroscopy system 100 can meet the target requirements specified by the medical professionals. After training, the fully trained neural models can be further optimized by the model optimization module 113 to produce optimized neural models.

Figure 2:
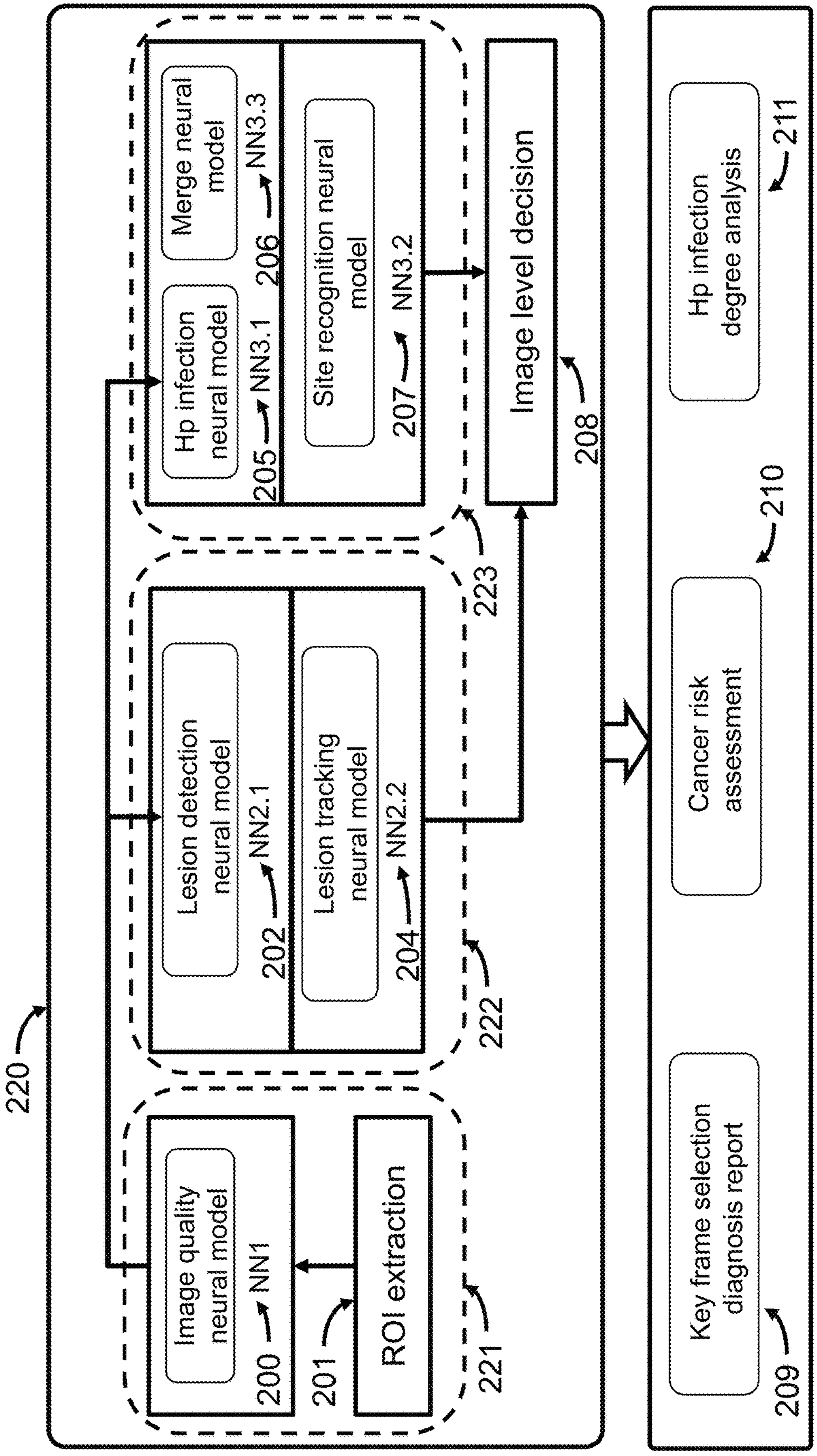
FIG. 2 shows a block diagram of an AI functions and image processing module in the computer-aided gastroscopy system of FIG. 1 according to some embodiments of the present disclosure.

The AI functions and image processing module 108 of FIG. 1 is further explained in FIG. 2. This module 220 further comprises three sub-modules, namely, the first module 221 for image control, the second module 222 for detecting lesions with a clear boundary and the third module 223 for detecting lesions without a clear boundary. All these three modules employ one or more neural models to process the gastric images. For notation clarity, we denote the neural model used in the first module as NN1, those in the second module NN2, and those in the third module NN3, respectively. As explained below, both the second module and the third module employ more than one neural model to do their analysis, we use sub-indices to denote them. For example, NN2.1 and NN2.2 denote the two neural models employed in the second module and NN3.1 and NN3.2 denote the neural models used in the third module.

The first module 221 further comprises a Region of Interest (ROI) module 201 and an image quality neural model NN1 (200) to perform image quality assessment. Its purpose is to filter out unqualified images in the gastric image sequence, thus saving time to do unnecessary inference on these bad images. The second module 222 employs a lesion detection neural model NN2.1 (202) to detect lesions with a clear boundary based on the object recognition technique. In addition to lesion detection, it also performs cancer identification. This second module 222 also includes a lesion tracking neural model NN2.2 (204) to do lesion tracking and key frame selection. The third module 223 makes use of a plurality of neural models for detecting HP infection and other types of lesions without a clear boundary. It consists of a feature extraction neural model NN3.1 (205), a site recognition neural model NN3.2 (207). The outputs of these two neural models are concatenated and sent to a merge neural model NN3.3 (206). The site information extracted from the site recognition neural model 207 is not only useful for the third module but can also be combined with the results of the second module to perform image level analysis 208.

The findings from all these three modules will be sent to a case-level analysis module which will further produce a key frame selection diagnostic report 209, cancer risk assessment 210 and HP infection degree analysis 211.

Neural network is a biologically inspired computational model. It consists of a plurality of nodes (or neurons) arranged in two or more layers. There are basically three categories of layers—an input layer, zero or more hidden layers and an output layer. The nodes in the input layer take in sensory input data. This may be in the form of a vector of real numbers, a two-dimension matrix such as pixel values of an image or even higher dimension data structure. The output layer provides the inference results of the neural network. When a neural network performs classification, each output node represents a class. The hidden layers are layers in between the input and output layers. Each node in the hidden or the output layer is connected to nodes in the previous hidden layer or the input layer; and each connection is associated with a real-number value, known as connection weight. In operation, each node first computes a weighted sum based on these weight values and the output values of the nodes in previous layers that it connects to, and then executes a function to obtain an activation value. This activation value is the output value of this node which will be sent to those nodes in the next layer that this node connects to. The function may be a Softmax function which is usually used for the last layer, a rectifier unit (ReLU), or simply the average or the max of the activation values of the nodes in the previous layer that this node is connected to. This constitutes a generic neural network architecture.

While a hidden node in a hidden or output layer may be fully connected to all the nodes in its previous hidden layer or the input layer, other neural architecture employs only partial connections. The former case is called a fully connect (FC) layer. In the popular Convolution Neural Network (CNN), which is typically used to process two dimensional digital images, a node in the hidden layer only connects to a small square grid of nodes in the previous layer. Typically, the grid size is 3×3, 5×5 or 7×7. The weight values of these connections specify a pattern that this hidden node is looking for and is generally referred to as the filter or the kernel of this hidden node. It is possible that more than one node in a hidden layer is connected to the same grid; but each of these nodes has a different filter, thus they are looking for different patterns from the same grid. These nodes can be stacked together so that the hidden layer can be concisely represented by a tensor of three numbers—two representing the grid size as mentioned above and the third representing the nodes that are stacked together.

A CNN neural model may have up to a hundred or more hidden layers. There are typically two categories of hidden layers—the convolution layer and the pooling layer. In the convolution layer, each node is looking for a particular pattern as mentioned before whereas in the pooling layer, all weights in the kernel are the same and the function of the node is either taking the average of all the grid values (AvgPooling) or the maximum of them (MaxPooling). Typically, the pooling layers are interspersed between one or more convolution layers. Another important parameter in defining a CNN is stride, which specifies the number of pixel shifts of the grids between adjacent nodes in the hidden layer.

Another neural architecture is a Recurrent Neural Network (RNN). In this network architecture, the hidden nodes are not only connected to nodes in previous hidden layer or input layer, but also have connections to their own output. As such, a RNN has the capability to remember its own processing states and it is capable of capturing order dependence in sequence prediction problems, such as time-series analysis. A specific class of RNN is the Long Short Term Memory (LSTM) neural model. A common LSTM unit consists of a cell, an input gate, an output gate and a forget gate. The cell remembers values over arbitrary time intervals and the three gates regulate the flow of information into and out of the cell. It is also possible to combine CNN and LSTM together. This is particularly useful for processing video as the CNN can be used to extract spatial information and the LSTM is useful for collecting temporal information.

There are a number of existing CNN models that are available for developers to use. Some examples are ResNet, CenterNet and Xception. Using these existing neural models can speed up the development time.

A neural network must be trained before it can be deployed. Training is to modify the connection weights of all the nodes. In one embodiment, the first step that one needs to do is to collect a dataset to train a neural network. For each sample in the dataset, one needs to assign a label to this sample. For a classification task, this becomes the class label of the sample. In some instances, an expert may be needed to examine a sample and assign a class label to it. When the number of samples is huge, this can be a tedious task. In one embodiment, training a neural network involves presenting the sample to the input layer, and comparing the output nodes at the output layer against the class label. The difference between the class label assignment and the activation values of the output nodes are expressed as a loss function and a training algorithm (such as the Back-Propagation algorithm) is invoked to adjust the weights of the connections so that after many iterations of training, the overall loss is reduced to a local minimum. After training, the neural network will have much higher discriminating power and the classification accuracy will be substantially higher than random choice.

In one embodiment, the output nodes of one neural network can be fed to the input nodes of a subsequent neural network. Alternatively, the output nodes of one neural network can be concatenated to the output nodes of a second neural network and then fed to the input nodes of a third neural network. As such, cascading one or more neural networks together in this manner creates a bigger neural network. We call the resultant neural network a composited neural model. Collectively, we use a symbol such as NN3 to denote the composited neural model and use subindices such as NN3.1, NN3.2, . . . , etc. to denote the individual neural model components.

Figure 3:
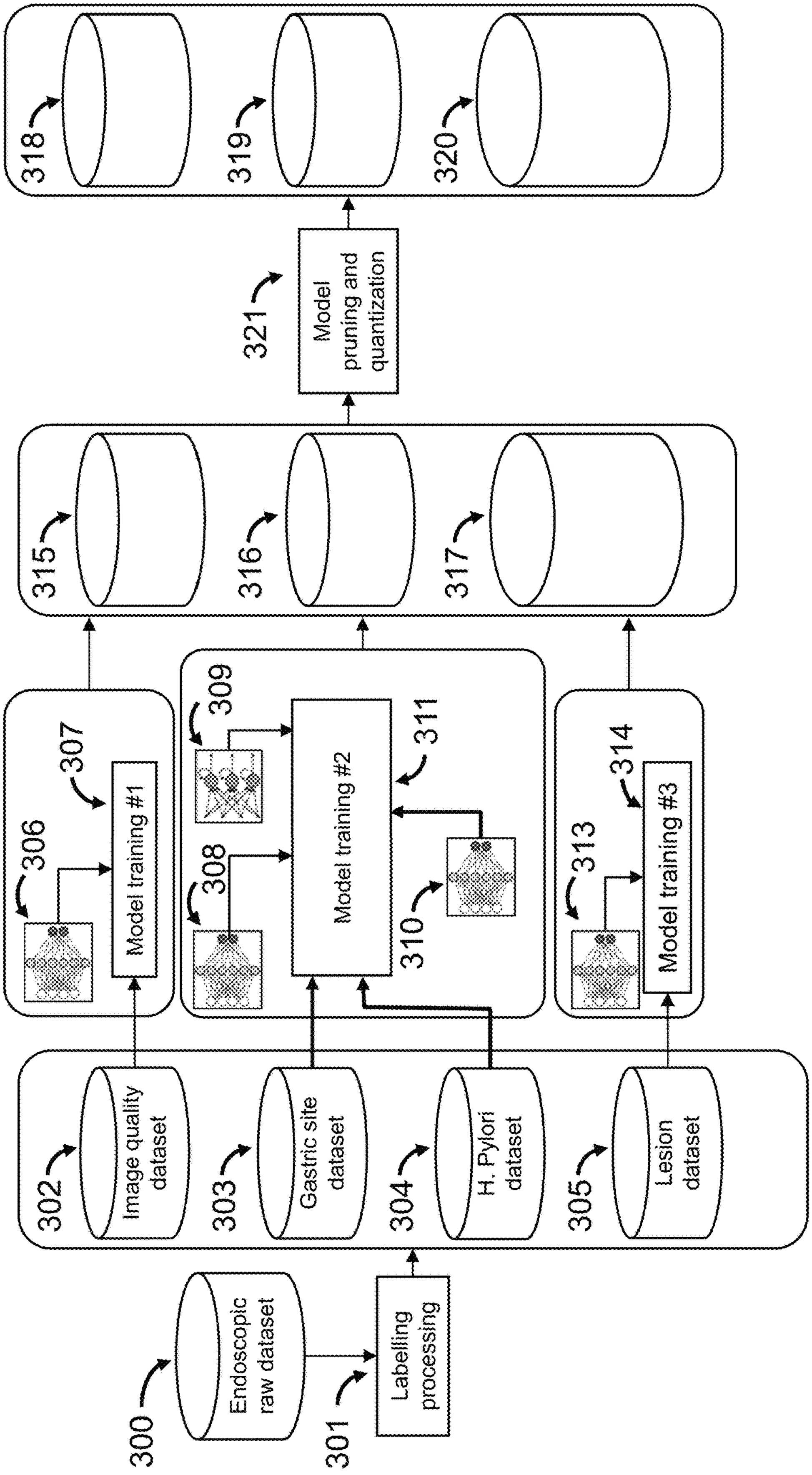
FIG. 3 shows the training process of various neural models according to some embodiments of the present disclosure.

FIG. 3 shows the training process of various neural models according to one embodiment of the present invention. Firstly, an endoscopic raw dataset 300 is collected. This raw dataset may comprise a plurality of different datasets. Through the labeling process 301, each sample in the raw dataset 300 is tagged with a label. The image quality dataset 302 is used to train the neural model NN1 of the first module using the model training #1 procedure 307. After training, a full image quality neural model 315 is obtained. Likewise, the gastric site dataset 303 and the *H. pylori* dataset 304 are used to train a plurality of neural models 308, 309 and 310 which are components of the composited neural model NN3 of the third module using the model training #2 procedure 311. This produces a full HP-plus-site neural model 316. The details of how each of the sub-models are trained will be discussed later. In the same fashion, the lesion dataset 305 is used to train the neural model both NN2.1 and NN2.2 of the second module using the model training #3 procedure 314 to obtain a full lesion detection neural model. While the respective full neural models produce the best detection and classification performance, they may require too many computing resources to run, and are not suitable for on-line processing. Hence these three full neural models are sent to the model pruning and quantization module 321 to prune the layer connections and quantize the connection weights. It then produces an optimized image quality neural model 318, an optimized HP-plus-site model 319 and an optimized lesion detection model 320, respectively. The optimized neural models speed up the inference while keeping the performances close to the respective full neural models. Table 1 shows the actual performances of the optimized neural models. As shown in this table, the target sensitivity and specificity values are specified by the medical professionals. The test values are the respective performance values of these optimized neural models. Table 1 shows that for the three classification and detection tasks, the optimized neural models all exceed the target values by large margins.

TABLE 1

Sensitivity and specificity performances of optimized neural models against user specified target values on three separate classification and detection tasks

| Model | Sensitivity (tested/target) | Specificity (tested/target) |
|---|---|---|
| HP infection classification | 0.87/0.8 | 0.95/0.8 |
| Lesion detection | 0.82/0.8 | 0.90/0.9 |
| Cancer detection | 0.79/0.65 | 0.92/Nil |

In this disclosure, we also refer the NN1 neural model as the image quality neural model; NN2 neural model as the lesion detection neural model and NN3 neural model as the HP-plus-site neural model. Whether these symbols refer to the full neural model or the optimized neural model will be specified in the context when these terms are used.

Classification of HP Infection and Lesions

We now discuss how the third module performs the classification of HP infection and lesions in details. This module is specifically designed to detect and classify lesions without clear boundary as the object detection model NN2 is not suitable for this task.

According to the Kyoto Classification of Gastritis, the *H. pylori* (HP) infection is classified into three phases: (i) non-gastritis or HP(−): the gastric mucosa is not infected by *H. pylori*, (ii) active gastritis or HP(+): the gastric mucosa is currently infected by *H. pylori*, and (iii) inactive gastritis or Past HP(+): the gastric mucosa was previously infected. When HP infection occurs, the gastric images exhibit certain symptomatic patterns. These patterns are used as features of the HP infection classifier to determine which of the aforementioned three categories the gastric images belong to. Table 400 in FIG. 4 shows a list of these features. The Kyoto Classification highlights six symptomatic patterns, which are indicated in the first 6 rows of table 400 and are grouped under reference label 401. On top of extracting these 6 features for HP detection, the feature set is expanded to include features that are useful in detecting and classifying other types of lesions without clear boundary as well. In this regard, features L6 and L7 (403) are used for classifying lesions unrelated to HP infection while feature L5 (402) and L8 (404) are used for classifying both HP infection and other types of lesions without clear boundary.

Thus, for the HP classifier, a total of 9 features (L0 to L8) is first extracted from the gastric images. The details on how to obtain these 9 values will be discussed in subsequent sections. Once obtained, they are sent to a tree classifier to determine which of the above three HP classes the gastric image belongs to.

Figure 5:
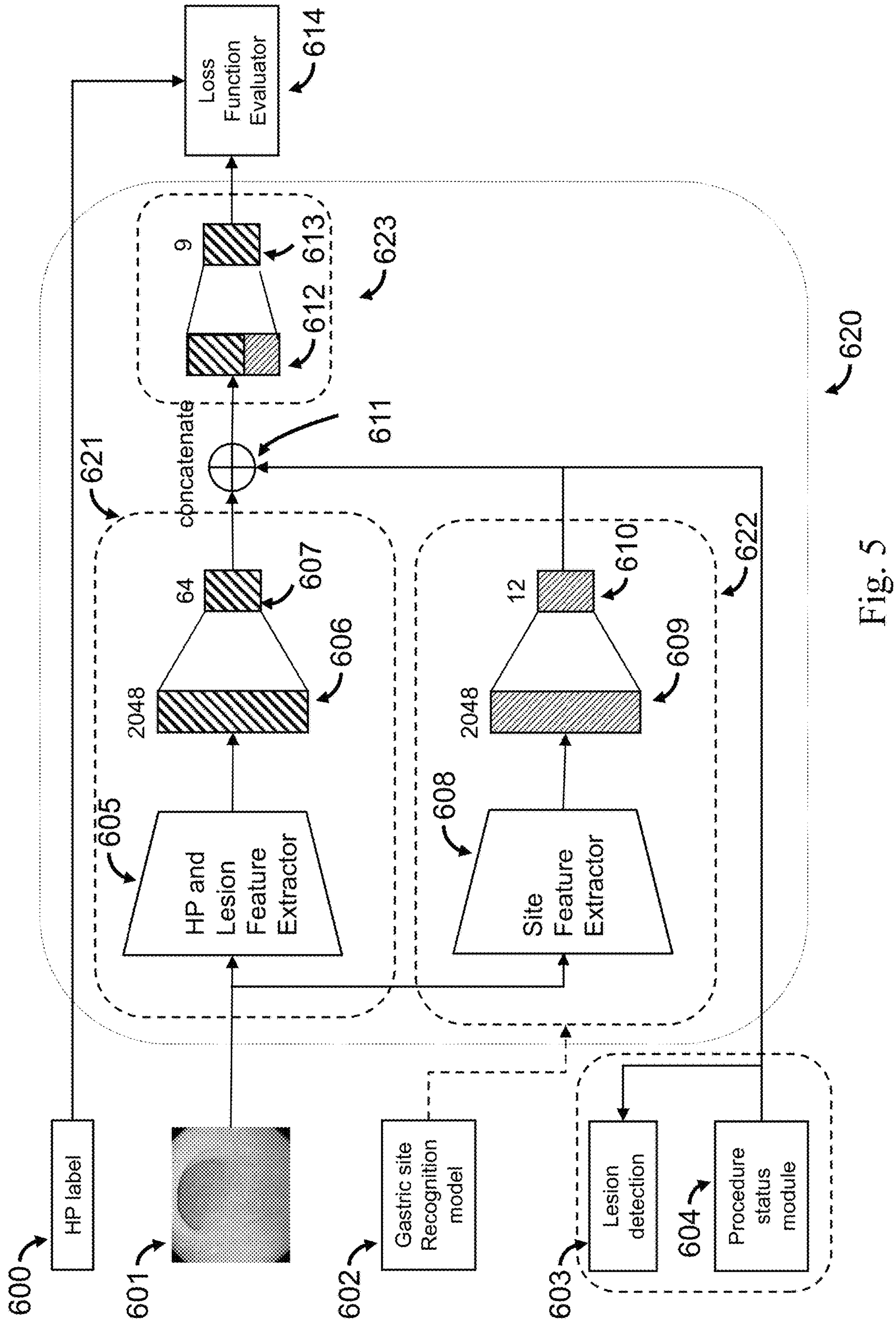
FIG. 5 shows a composited neural model of the third module and how it is trained according to one embodiment of the present disclosure.

FIG. 5 reviews the major components of the third module, which performs HP infection feature extraction and site recognition. The neural network NN3 (620) is a composited neural model that combines three neural models together, namely NN3.1 (621), NN3.2 (622) and NN3.3 (623). NN3.1 (621) is designed for extracting features of HP infection and other types of lesions without clear boundary and it consists of a HP and Lesion Feature Extractor 605. Its output layer is a vector of 2048 elements or 2048×1 channels (606). This vector is compressed to a vector of 64 elements at the next layer (607). In one embodiment, the connections between layer 606 and layer 607 are a fully connected network. In another embodiment, a 1×1 convolution kernel is used.

NN3.2 (622) is a special neural network designed for site recognition. It consists of a Site Feature Extractor 608 whose output layer is a 2048×1 element vector 609 which is further compressed to a 12-element vector at the next layer 610. The output nodes of layer 610 are concatenated with the output nodes of layer 607 at the concatenation gate 611 to become the input nodes 612 of a merge neural network NN3.3 (623). The input size of NN3.3 (623) is therefore (64+12=76) elements. This input layer 612 is fully connected to the output layer 613 which is a vector of 9 elements. These 9 elements correspond to the 9 features L0 to L8 in table 400 of FIG. 4.

In operation, a gastric image 601 is sent to the HP Feature Extractor 605 as well as the Site Feature Extractor 608. Both neural networks NN3.1 (621) and NN3.2 (622) process the same image simultaneously; NN3.1 (621) focuses on extracting information of HP infection and other types of lesions without clear boundary, while NN3.2 (622) performs site recognition. The site information provides additional information for HP detection hence by concatenating the outputs of NN3.1 (621) and NN3.2 (622), the merge neural network NN3.3 (623) combines both information sources together so that the sensitivity of HP infection detection is improved.

In one embodiment, both the HP Feature Extractor 605 and the Site Feature Extractor 608 are multi-layer CNN neural models. In a further embodiment, they are the Xception CNN model.

These neural models are trained as follows. In one embodiment, NN3.2 (622) is pre-trained. The entire neural model is copied from the gastric site recognition model 602. On the other hand, NN3.1 (621) and NN3.2 (623) are trained with the connection weights in NN3.2 (622) fixed. These two neural models are trained by first presenting the images 601 to both the input layers of NN3.1 (621) and NN3.2 (622). HP label 600 provides the label corresponding to this image and is sent to the loss function evaluator 614. The loss function evaluator 614 compares the outputs of NN3.3 (623) against this HP label 600 and uses a pre-defined loss function to evaluate a loss value. The training procedure adjusts all the connection weights in NN3.1 (621) and NN3.3 (623) to minimize this loss value while the connection weights of NN3.2 (622) are kept unchanged. In one embodiment, the Binary Cross Entropy (BCE) with Logits loss function is adopted in this implementation.

It is observed that the composited neural model NN3 is able to learn the correlation between the HP infection features and the gastric site locations. Thus site-assisted neural model NN3 is able to increase the sensitivity of HP infection detection by 5.6% in one experiment while keeping the specificity unchanged.

The site information from NN3.2 (622) not only helps in HP infection classification but can also be used to post-process the results from lesion detection and to determine the operation procedure status of the gastric examination process. In one embodiment, the site information can be used to: (1) determine start-stop operation procedure, and (2) reduce false positives of HP infection classification and lesion detection. As an example, if the procedure is at a stopping stage, then the system still needs to perform AI inference as usual so that false positives of HP classification and lesion detection may be reduced. As another example, if the endoscope is in the duodenum tract inferred from the site information, then the system may ignore any HP features from the model, thus reducing the false positives. As such, the outputs of NN3.2 (622) are directed to the lesion detection neural model (603), which is a neural model in NN2 of the second module; and also, the procedure status module 604.

As mentioned previously, site information is useful to many modules in this system. The gastric site recognition model 602 is a neural model that is trained to identify the site location in a gastric image. In one embodiment, the site locations are shown in a table in FIG. 6. Each of the entries in this table is related to a location in the upper gastrointestinal track. The gastric site dataset contains a large set of images annotated with site labels as shown in FIG. 6 to train the site recognition neural models.

Figure 7:
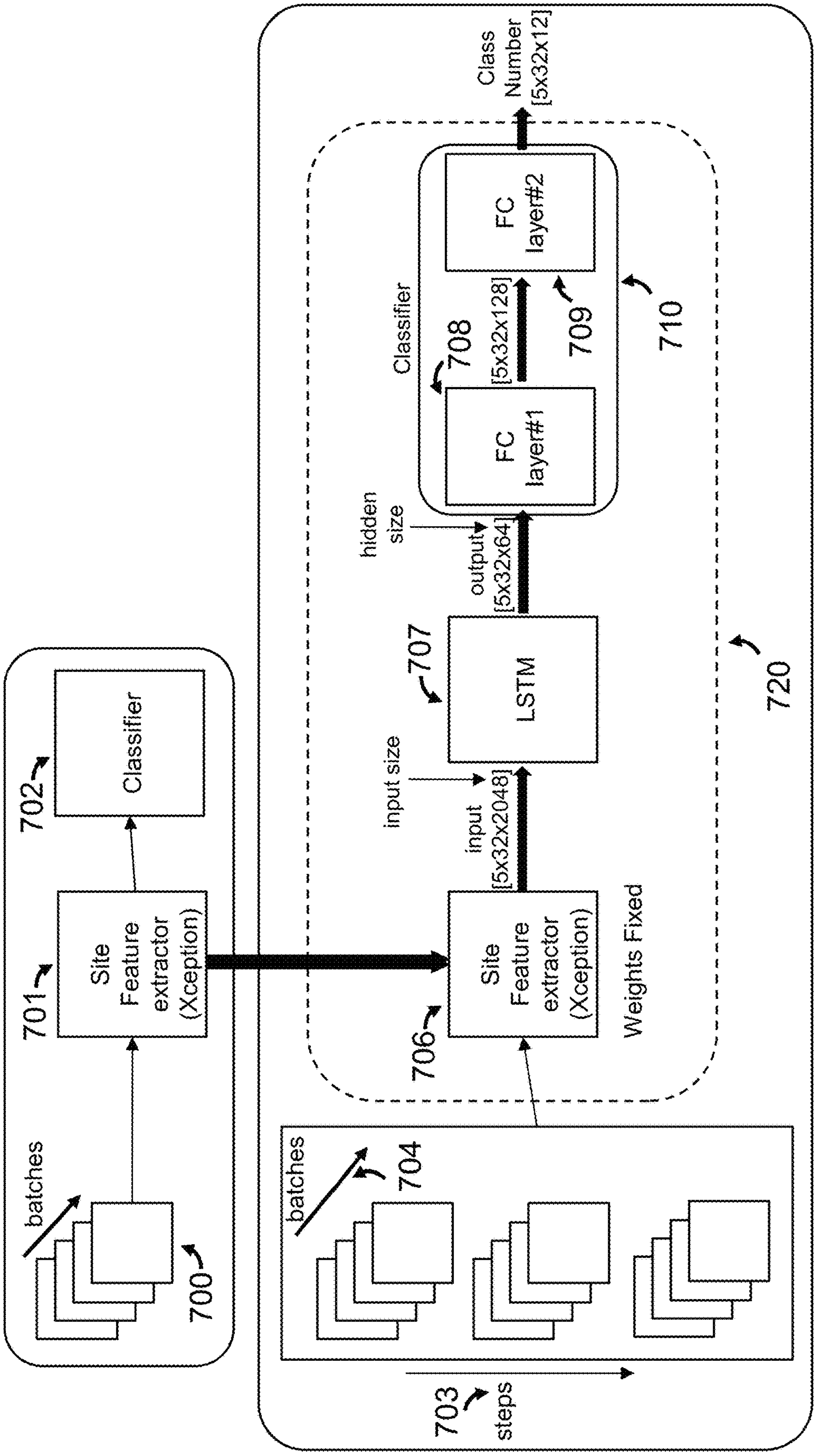
FIG. 7 illustrates the various components of the site recognition model and how it is trained in one embodiment of this invention.

FIG. 7 illustrates an alternative embodiment of the site recognition model and how this alternative site recognition neural network is trained in one embodiment of this invention. The first step is to train an auxiliary neural network 701 which serves as a site feature extractor. This in itself is a CNN. In a further embodiment, it adopts the Xception neural model. The output of this CNN is a vector of 2048 channels and they are connected to a classifier neural network 702. Both neural networks 701 and 702 are trained together to recognize site labels as shown in FIG. 6. A cumulative batch of gastric images 700 from the gastric site dataset is used to train this composite neural model.

After this step of training, the auxiliary neural network 701 is retained and copied to a composite neural model 720. Composite neural model 720 comprises a site feature extractor model 706, a LSTM model 707 and a final neural model 710. Site feature extractor 706 is a direct copy of the auxiliary neural network 701 which extracts site features and its connection weights will not be updated when the other two neural models are trained. To train the LSTM model 707 and the final neural model 710, a sequence of batch units is first prepared. In one embodiment, a pseudo video that emulates an actual gastric video image sequence is first created based on the labelled gastric images drawn from the gastric site dataset. (Please refer to the paragraphs below and also FIG. 8 for the generation of a pseudo video image sequence). From this pseudo video, five consecutive images are grouped together to form a batch unit. In an embodiment, five gastric images are grouped along the time step direction 703 to form a batch unit. Then thirty two of these batch units are grouped together to form a batch group along the batches direction 704. During training, the site feature extractor 706 produces a feature vector of 2048 channels for each image. Thus, for one batch unit, this site feature extractor 706 produces an output tensor of [5×1×2048] elements, and for a batch group with thirty-two batch units, it produces an output tensor of [5×32×2048] elements. This is fed to the LSTM model 707, which captures the temporal information from the gastric image sequence and outputs a tensor of [5×32×64] elements. This output tensor serves as input to the final neural model 710. This neural model has a first fully connected layer 708 coupled to another fully connected layer 709. The output of this neural model, which is also the output of the composite neural model 720 is a tensor of [5×32×12] elements. The last dimension is the number of site labels and each element in this dimension corresponds to a site label as shown in the table of FIG. 6.

It would be appreciated that FIG. 7 only illustrates an exemplary method of training the composited neural model 720. In this example, labelled gastric images are arranged into batch unit and then to batch groups with a sequential index in preparation for training. The batch size of 32 and the number of batch units in a batch group, i.e. 5 are adopted here for illustration only. Other values can be used.

It would be appreciated that the LSTM model 707 is capable of capturing temporal information. Hence, the training data needs to exhibit the temporal information for the LSTM to capture. In an actual gastroscopy operation, the entire operation is captured in a video which contains the temporal information. However, in order to use this video to train the LSTM model 707, each frame of this video needs to be assigned a site label as shown in the table of FIG. 6. This has to be done by an expert in this field and labelling is very time consuming and tedious. On the other hand, a gastric site dataset is available, each image in this dataset has already been labelled. However, these are still images which do not carry any temporal information. Thus, a method of creating pseudo videos from these still images is developed and is disclosed as follows.

Figure 8:
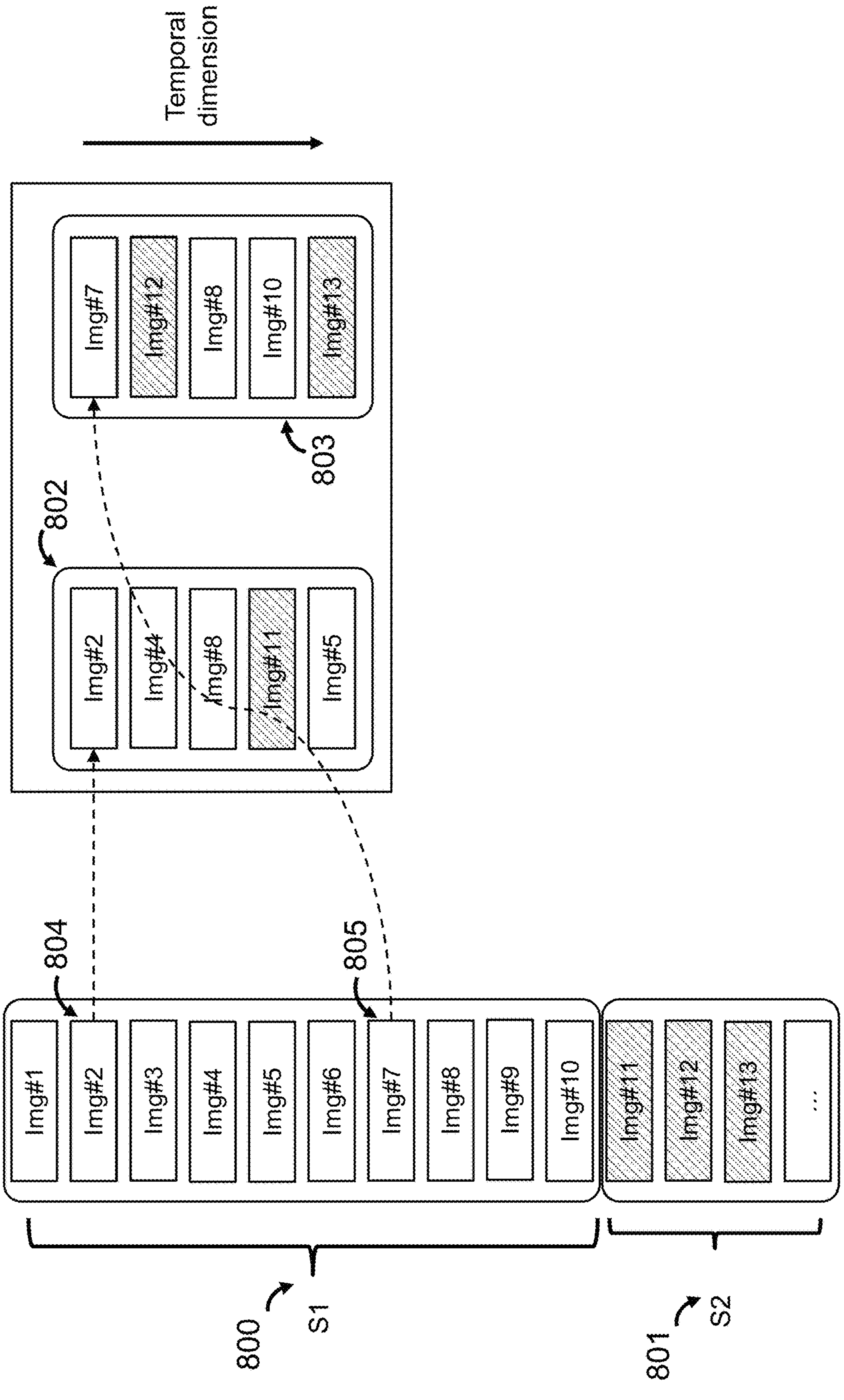
FIG. 8 illustrates a method of creating the pseudo video sequence in one exemplary embodiment of the present disclosure.

Referring now to FIG. 8, an exemplary embodiment is given to illustrate a method of creating the pseudo video sequence. In this example, we assume that there are only two labels S1 and S2 in the gastric image dataset and we want to create two batch units. The first step is to sort all the labelled images in the gastric site dataset so that images of the same labels are grouped together, and the groupings are sorted in accenting order. As an example, images with label S1 are grouped together as the first label group 800 and images with label S2 are the second label group 801, which is attached to the end of the first label group 800 to form a long chain of sorted labelled images. Next, an image (in this case Img #2 804) from the first label group 800 is randomly selected and inserted as the first labelled image in the first batch unit 802. Then using this image as an anchor, other images are selected and inserted into the first batch unit 802. To this end, four random numbers are generated. Noted that when generating the random numbers, the random range can be adjusted. When the range is small, the probability of selecting samples within the vicinity of the anchor image is higher. Therefore, the selected image will likely have the same label as the anchor image. On the other hand, when the random range is high, an image from a different label group may be selected. With four random numbers generated from four different random ranges, it is possible to generate a sequence of images whose labels are mostly the same as that of the anchor image but also contain images with different labels interspersed randomly in the first batch unit 802. In a similar manner, the second batch unit 803 is constructed. Here the anchor image is Img #7 805 in this example. Notice that in this example, Img #7 805 is closer to the end of the first label group than Img #2 804. Therefore, the second batch unit 803 has more images selected from the second label group 801 compared to the first batch unit 802. In this way, the sequential ordering of the composed images in both batch units becomes a pseudo video that is capable of emulating a video image sequence exhibiting site boundary transitions. In other words, the temporal information at site transitions is artificially created from still labelled images and such site transition information can then be used to train the LSTM model.

It would be appreciated that FIG. 8 only illustrates an exemplary method of generating pseudo video image sequence for training. The same method can be generalized to accommodate more than two site labels and generate more than two batch units.

In one embodiment, both the site feature extractor 701 and 706 adopt the Xception neural model. While the site feature extractor 706 captures the spatial information of the gastric image, the LSTM model 707 captures the temporal aspect of the gastric image, so together this composite neural model 720 extracts both spatial domain and time domain information from the gastric image sequence.

Figure 9:
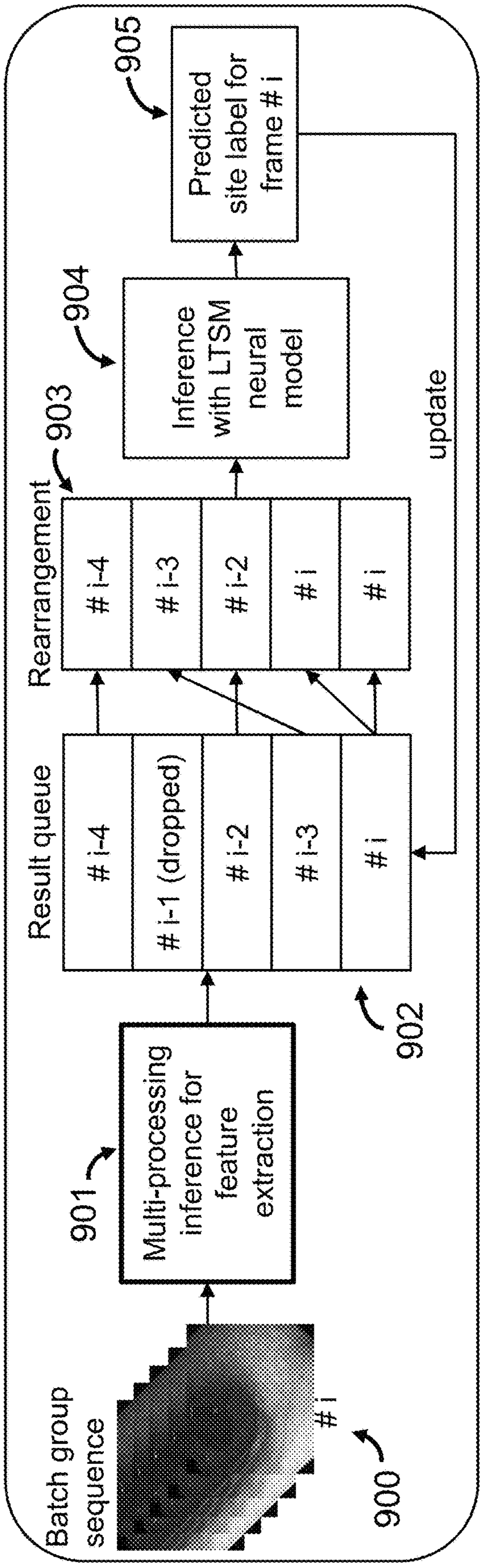
FIG. 9 shows an exemplary instance of training the site recognition neural model according to one embodiment of the present disclosure.

In one embodiment, the site feature extractor 706 in FIG. 7 takes the longest time to execute. It needs to extract features for each image in a batch unit. To speed up this process, each batch unit in a batch group can be performed in parallel in a system equipped with one or more coprocessors such as a GPU card, and the results are put into a result queue. However, each subtask may finish at a different time, and this may create an out-of-sequence problem as illustrated in FIG. 9. Referring to FIG. 9, a multi-processing feature extraction step 901 creates subtasks for each batch unit from a batch group sequence 900 and these subtasks are distributed to the one or more coprocessors such that they are executed in parallel. The results are placed in the result queue 902. However, some subtasks may finish earlier than others, so when they are inserted into the result queue, they may be out of the intended sequential order. Moreover, there may be instances when a subtask may not generate any result. In both cases, it causes the batch units in the result queue 902 not to be arranged in its intended sequential order and hence they need to be rearranged in step 903 before they are sent to the LTSM model to train. After re-arranging, they can be sent to the LTSM model and performs LTSM model inference. The output of LTSM inferencing is a prediction of site label for the $i^{th}$ sequence order in step 905 and this can be inserted back to the result queue.

The composite neural model 720 can be deployed to a practical application environment. In a practical deployment, a sequence of gastric images is presented as input to this composited neural model 720 instead of a group of sequential batch units. In essence, this is equivalent to setting the batch size to one and while the LSTM model can produce an output of 5 sequence-steps, only the latest time-step is taken so the output of the composite neural model 720 is a vector of 12 elements, each of which corresponds to a site label as shown in FIG. 6.

With this arrangement, the composite neural model 720 can replace NN3.2 (622) in FIG. 5. Since the composite neural model 720 makes use of the LSTM model 707 to capture temporal information, it further helps the HP infection classifier to improve its accuracy. Table 2 below shows the accuracy improvement. As shown in the table, adding the LSTM model 707 to the Xception site feature extractor 706 boosts the accuracy of HP infection classification from 94.6% to 97.4%; a 2.8% improvement.

TABLE 2

Improvement of Accuracy after incorporating the LTSM model

| Model type | Accuracy |
|---|---|
| Xception alone | 94.6% |
| Xception + LTSM | 97.4% |

Figure 10:
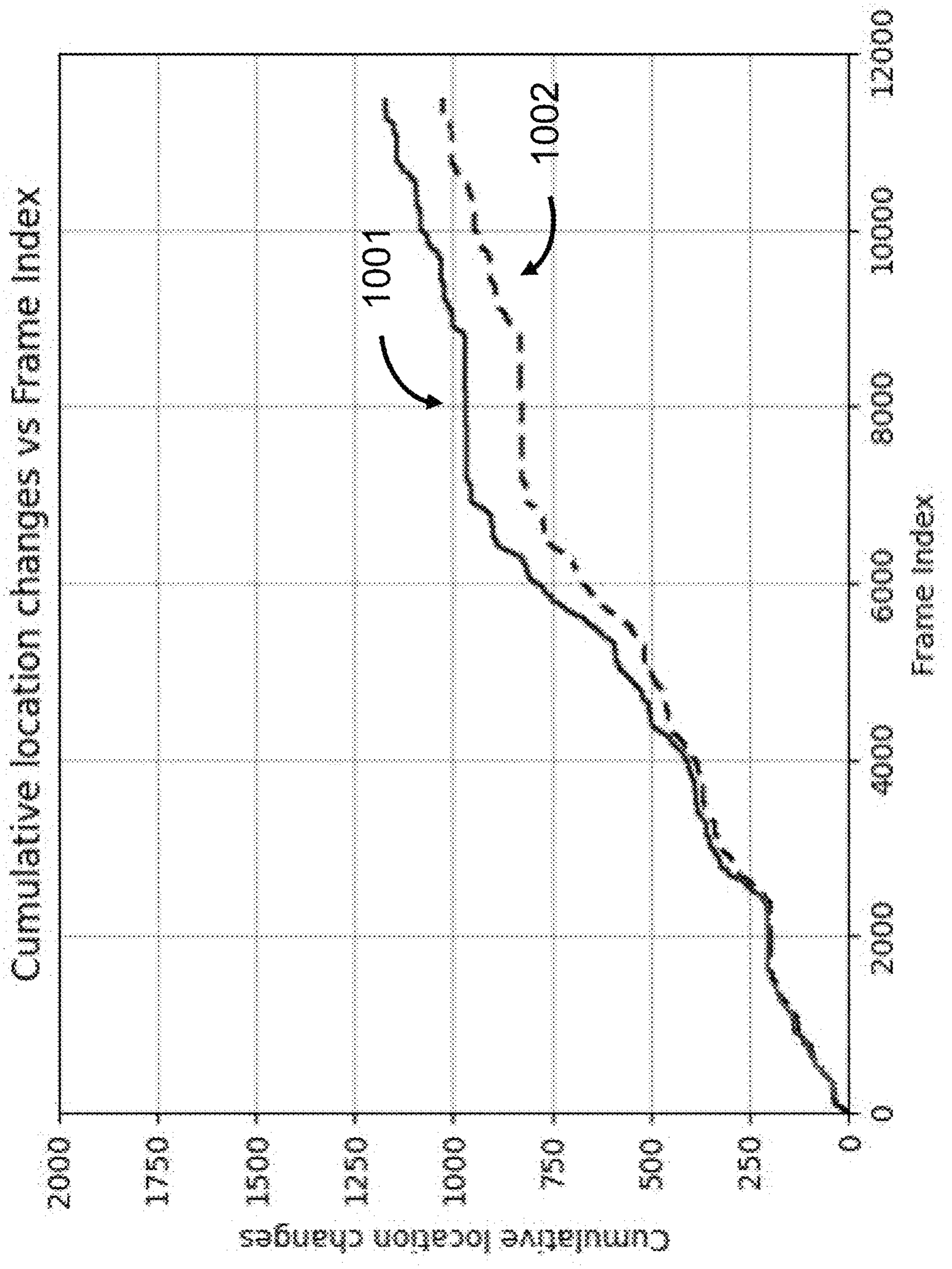
FIG. 10 shows an exemplary experimental result on cumulative location changes vs. frame index according to one embodiment of the present disclosure.

In addition to improving the HP detection accuracy, the composite neural model 720 also reduces the number of false positives in detecting site transitions in a gastric video. FIG. 10 shows the results of one experiment. In this figure, the horizontal axis represents the frame index in a video sequence, while the vertical axis is the cumulative location changes or site transitions. The two curves in this figure show the differences in cumulative location changes in a typical gastric video. Curve 1001 is obtained without the use of the LSTM 707 model while curve 1002 is obtained by using the LSTM to capture the temporal site transition information. This figure clearly shows that with the help of the LSTM 707 model, the number of false positions on site transitions is greatly reduced.

Preprocessing

Preprocessing is a step to prepare the gastric images to a form that can be processed by various neural models. Nowadays, gastroscopy instrument comes from different manufacturers and different brands. Each of them may use a different camera with different pixel resolutions. This may range from less than 384×384 pixels to more than 3840×2180 pixels. Most of them are color cameras, so the total number of pixels is three times the resolution. On the other hand, each neural model adopted in this system requires an input image dimension of a specific size. For example, the Xception model works on a color image of 299×299×3, the CenterNet requires an input of 384×384×3 while the ResNet model handles an input of 224×224×3. Hence there is a need to convert the incoming gastric images of different resolutions to a format that is suitable for each of the neural models; and this is the task of preprocessing.

Figure 11:
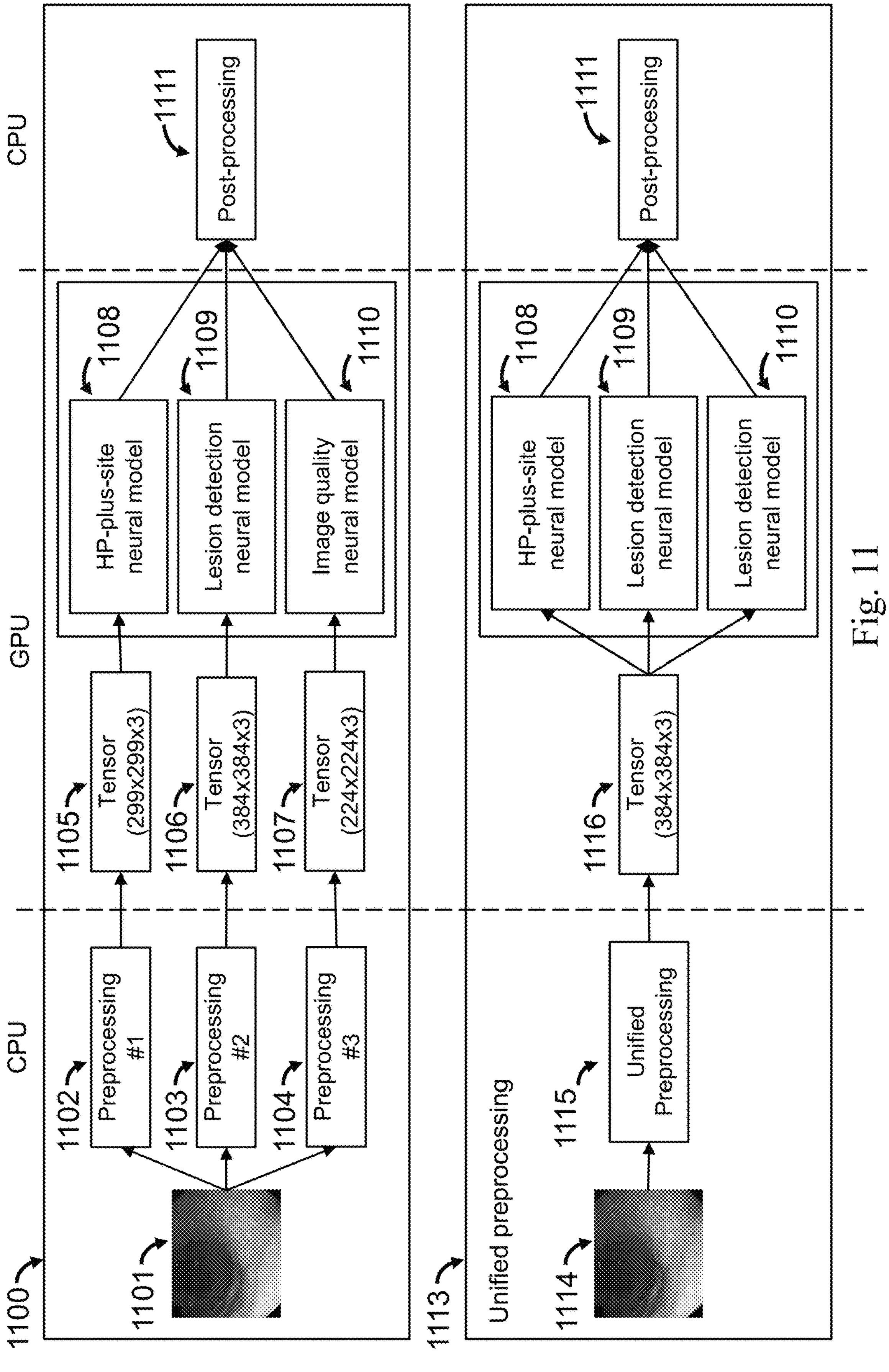
FIG. 11 shows two different preprocessing methods according to some embodiments of the present disclosure.

Referring now to FIG. 11 and as discussed earlier, the computer-aided gastroscopy system uses three neural models mentioned to process the gastric images. A conventional endoscopic image analysis scheme 1100 would employ three different preprocessing modules 1102, 1103 and 1104 to process the input gastric image 1101. For preprocessing module #1 1102, it converts the input image to a tensor of [299×299×3] dimension 1105 to be fed to the HP-plus-site neural model 1108. Likewise, the preprocessing module #2 1103 produces a tensor of [384×384×3] dimension 1106 to satisfy the input requirement of CenterNet, which is used in the lesion detection neural model 1109. Lastly, the preprocessing module #3 1104 generates a tensor of [224×224×3] for the image quality model 1110. The outputs of the three neural models will be sent to the post-processing module 1111 for further processing.

This convention approach is clearly not efficient as it requires three separate preprocessing modules. While each of these modules produces a unique output image dimension specified by its recipient, most of the processing in these individual preprocessing modules are the same, so it would be preferable to consolidate them to save computational time and resources. As such, a unified preprocessing endoscopic image analysis scheme 1113 is developed whereby it adopts a unified preprocessing module 1115 to process the gastric image 1114 and produce an output tensor 1116 of [384×384×3] dimension. This same tensor serves as input to the respective neural models 1108, 1109 and 1110. The outputs of these three neural models will be sent to the same post-processing module 1111 for further processing.

Since the output tensor dimension 1116 of the unified preprocessing unit 1115 may not be the same as what is required by the subsequent neural models, the neural models may need to adjust its internal architectural parameters so that it can accommodate the output tensor dimension 1116. Once the internal architectural parameters are changed, a neural model may produce an output tensor dimension that is different from the original one. On top of that, the performance may degrade. It would therefore be desirable to keep the output tensor of the neural model the same and its performance not degraded so as not to affect any downstream processing. Hence the neural architecture parameters need to be changed.

An exemplary embodiment is given here on how to adjust the neural architecture parameters to accommodate the change of input tensor dimension while keeping both the performance and the output tensor dimension the same. In this embodiment, the Xception neural model is used to illustrate the essential concept. The Xception neural model is a CNN model that is used to extract site recognition features in this application. This 71-layer neural model is organized in three main sections, namely the Entry flow, the Middle flow and the Exit flow. In one embodiment, only the Exit flow section is modified to satisfy the aforementioned criteria. In the original Xception architecture, the input tensor is [299×299×3] and the output tensor is a vector of 2048×1 dimension. The intermediate input tensor to the Exit flow section of the Xception model is [19×19×728]. If the input tensor is changed to [384×384×3] to accommodate the output tensor 1116 of the preprocessing unit 1115, the input tensor of the Exit flow section becomes [24×24×728] since the first two dimensions of the input tensor at the Entry flow section is bigger. Thus, some of the parameters in the Exit flow section are modified to keep the performance and the output tensor the same.

Figure 12:
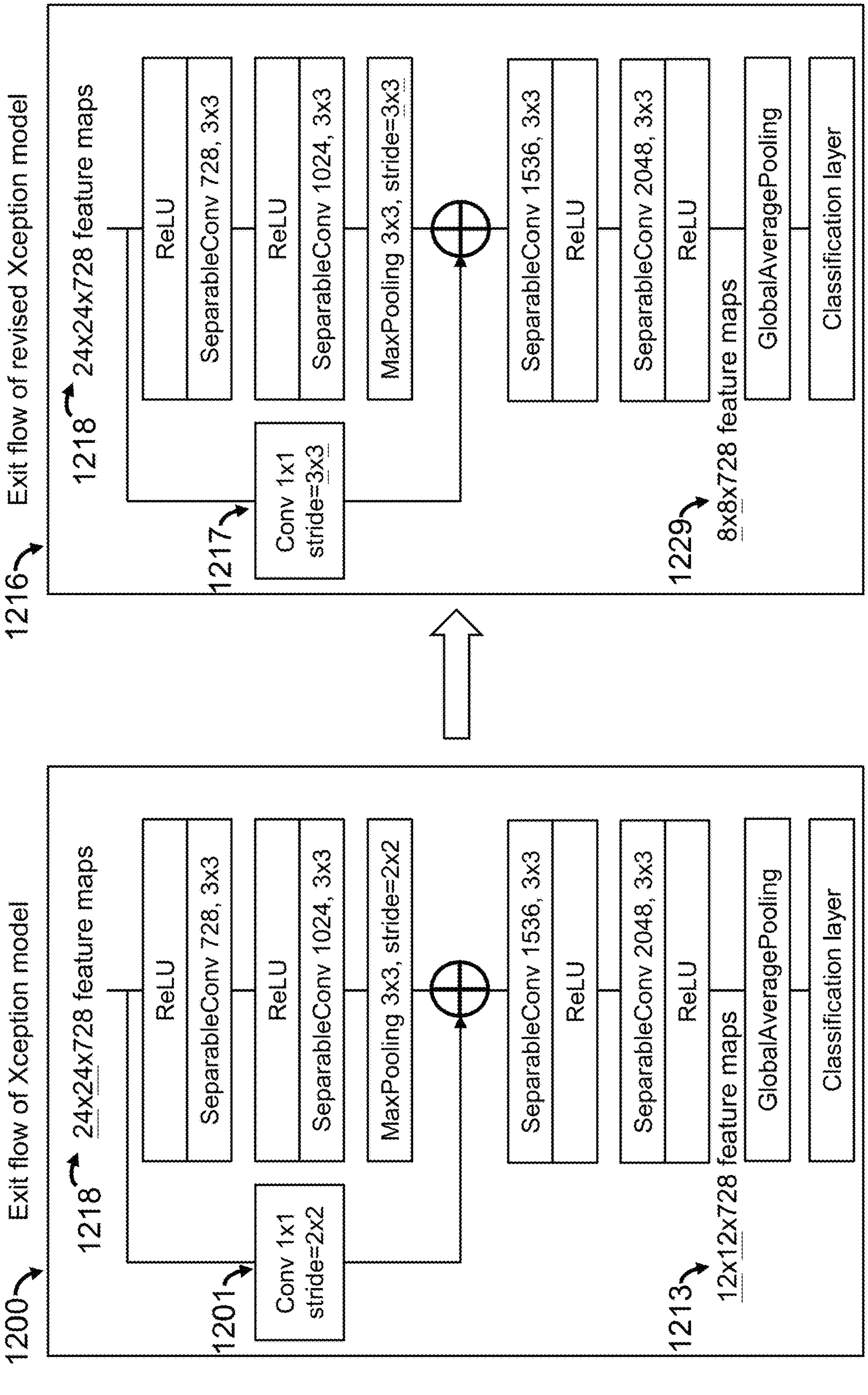
FIG. 12 shows an example of modifying a neural architecture according to one exemplary embodiment of the present disclosure.

Referring now to FIG. 12, reference label 1200 shows the original Exit flow architecture of the Xception model while reference label 1216 shows the revised Exit flow architecture that produces the same output vector as desired. As mentioned earlier, when the input tensor of the Entry flow is changed to [384×384×3], the input tensor 1218 at the Exit flow layer becomes [24×24×728]. In the original Exit flow model 1200, it produces a feature map 1213 of [12×12×728] tensor dimension. Notice that a feature map with a larger size is undesirable as it will lose more information after global pooling. By changing the block 1201 that performs 1×1 convolution with a stride of 2×2 to the block 1217 that performs 1×1 convolution with a stride of 3×3, the revised Exit flow 1216 produces a feature map 1229 of [8×8×728] tensor dimension. This effectively minimizes information loss.

The aforementioned example illustrates by example the idea of adjusting the neural architecture to accommodate different input tensor sizes. It would appreciate that for different neural architectures, different parameters may need to be changed to achieve the desired result but based on the teaching disclosed in this specification, those skilled in the art would be able to apply this same idea to solve their specific problem.

Compared to the convention preprocessing approach as shown in 1100 of FIG. 11, Unified preprocessing 1113 achieves much faster preprocessing time. The following table compares the preprocessing time required between the conventional approach and the unified preprocessing approach.

TABLE 3

Comparison of Preprocessing time between Separated Preprocessing vs Unified Preprocessing

| Image resolution | Separated preprocessing (in millisecond) | Unified preprocessing (in millisecond) |
|---|---|---|
| 3840 * 2160 | 28.7 | 10.6 |
| 1920 * 1080 | 29.0 | 11.1 |

Referring to this table, it shows that the unified preprocessing approach can reduce the preprocessing time by roughly one-third for both image sizes. This experiment was carried out on a computer with an Intel Core i7-7800X CPU running at a 3.5 GHz clock rate.

As mentioned earlier, different makes and brands of gastroscopy instruments use different cameras to produce gastric images. The resolutions of these cameras vary widely—from low resolution 342×372 pixels to very high resolution 3840×2160 pixels. In unified preprocessing, the standardized output is a tensor 1116 of the [384×384×3] dimension. Hence no matter what the camera resolution is, the unified preprocessing module 1115 is to resize the input gastric image to a standardized output dimension.

Figure 13:
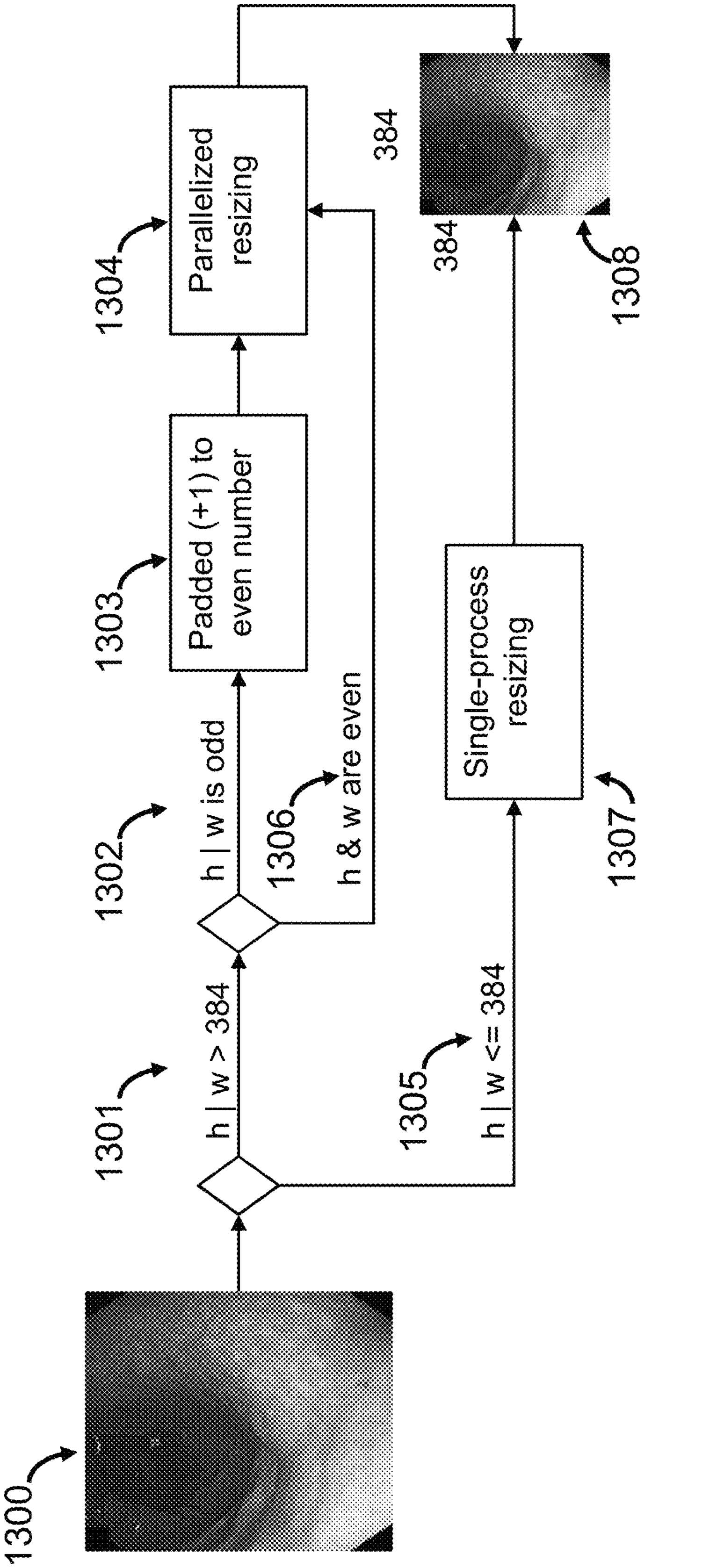
FIG. 13 shows a flow diagram on preparing an image for re-sizing according to one embodiment of the present disclosure.

FIG. 13 shows a flow chart of how this is done. Referring to this figure, if either the height or width of the input gastric image 1300 is below 384 pixels, it follows the path 1305 to direct that image to do single-process resizing 1307, which will re-size the image to 384×384 pixels.

If either the height or the width of the gastric image 1300 is higher than 384, it takes on the path 1301. Then it further checks if either the height or the width of the gastric image 1300 is an odd number. If it is, then the path 1302 is taken and the gastric image is padded with either a row of zeros or a column of zeros so that the resultant image has even numbers of rows and columns. The resultant image is then sent to a parallelized resizing module 1304 for resizing. If both the height and the width of the original gastric image 1300 are even numbers, then the path 1306 is taken and the image will be sent directly to the parallelized resizing module 1304. After resizing, an image 1308 of 384×384 pixels is obtained.

Figure 14:
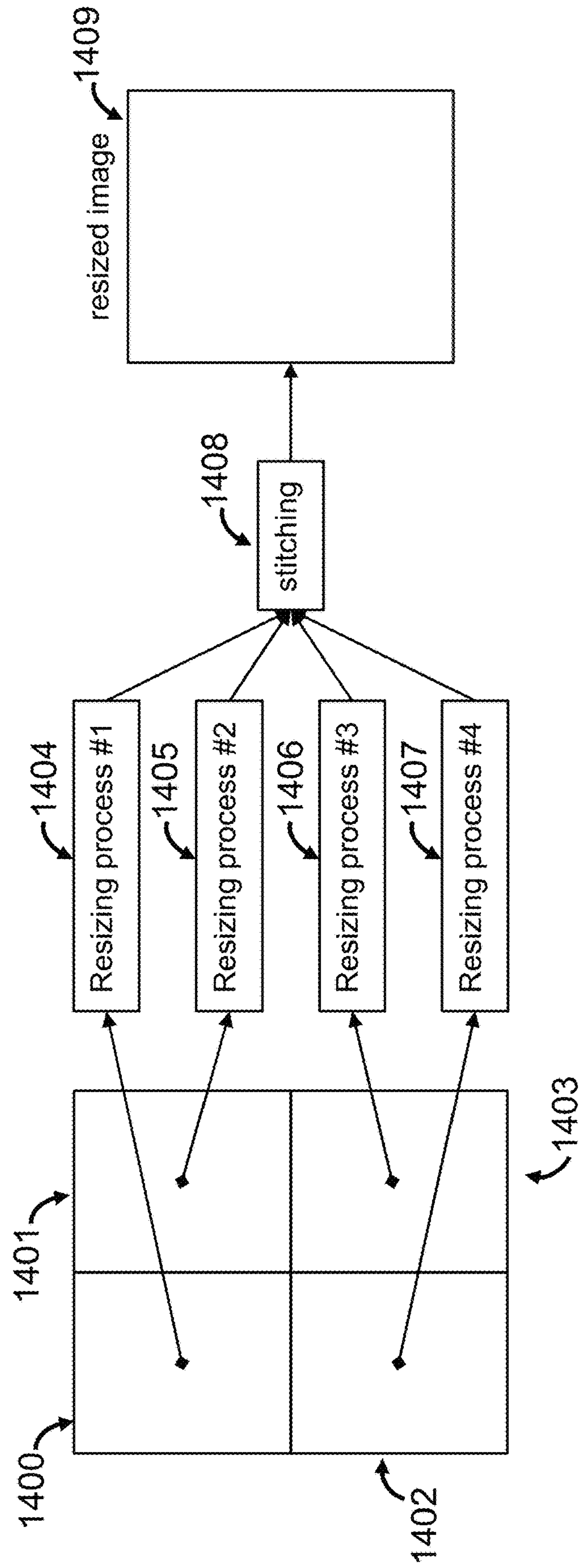
FIG. 14 shows a method of performing parallel re-sizing on a gastric image according to one embodiment of the present disclosure.

FIG. 14 illustrates in detail how the parallelized resizing module 1304 in FIG. 13 is performed. The input image is first partitioned into four quadrants 1400, 1401, 1402 and 1403. Each quadrant is sent to a resizing process 1404, 1405, 1406 and 1407 respectively. The results of these four resized quadrants are then stitched together at 1408 to produce a resized image 1409. In this method, overlapping cropping is avoided, thus saving computation time.

If the computer-aided gastroscopy system is equipped with coprocessors such as Graphic Processing Unit (GPU) cards, then the resizing process can be performed in parallel to speed up the resizing process. In this case, the main CPU of the computer-aided gastroscopy system can distribute tasks initiated by the resizing process 1404, 1405, 1406 and 1407 to the coprocessors when they are idling so that these processes can run in parallel.

The following table shows the speed-up performance between a single process resizing vs four processes working in parallel.

TABLE 4

| Speed-up performance between a single process resizing vs. four processes working in parallel Image resizing time | | | |
|---|---|---|---|
| Image resolution | Interpolation method | Single process (ms) | Four processes (ms) |
| 3840 × 2160 * | area relation | 14.5 | 7.8 |
| 1243 × 1080 | area relation | 3.4 | 1.9 |
| 342 × 372 | bilinear | 0.33 | — |

* 4K image output from OEV321UH: 32-Inch LCD Monitor Optimized for Olympus Endoscopy Systems. CPU: Intel(R) Core(TM) i9-9900K CPU @ 3.6 GHz Referring to this table, it clearly shows that the resizing time can be roughly cut in half using parallelized resizing. If the gastric image size is smaller than 384×384 in either dimension, then there is no need to do parallelized resizing as a single process system can resize the image in less than half of a millisecond. This experiment was carried out on a computer with an Intel Core i9-9900K CPU running at a 3.6 GHz clock rate.

Hardware Configuration

Deep neural models demand a substantial amount of computational resources to run. It is advantageous to explore parallel processing techniques to reduce the run time. Nowadays, it is easy to add one or more coprocessors such as Graphic Processing Unit (GPU) cards to a personal computer to boost the overall computational power. The computer-aided gastroscopy system is developed to take advantage of this trend and is capable of utilizing all available hardware facility to speed up the response time.

Figure 15:
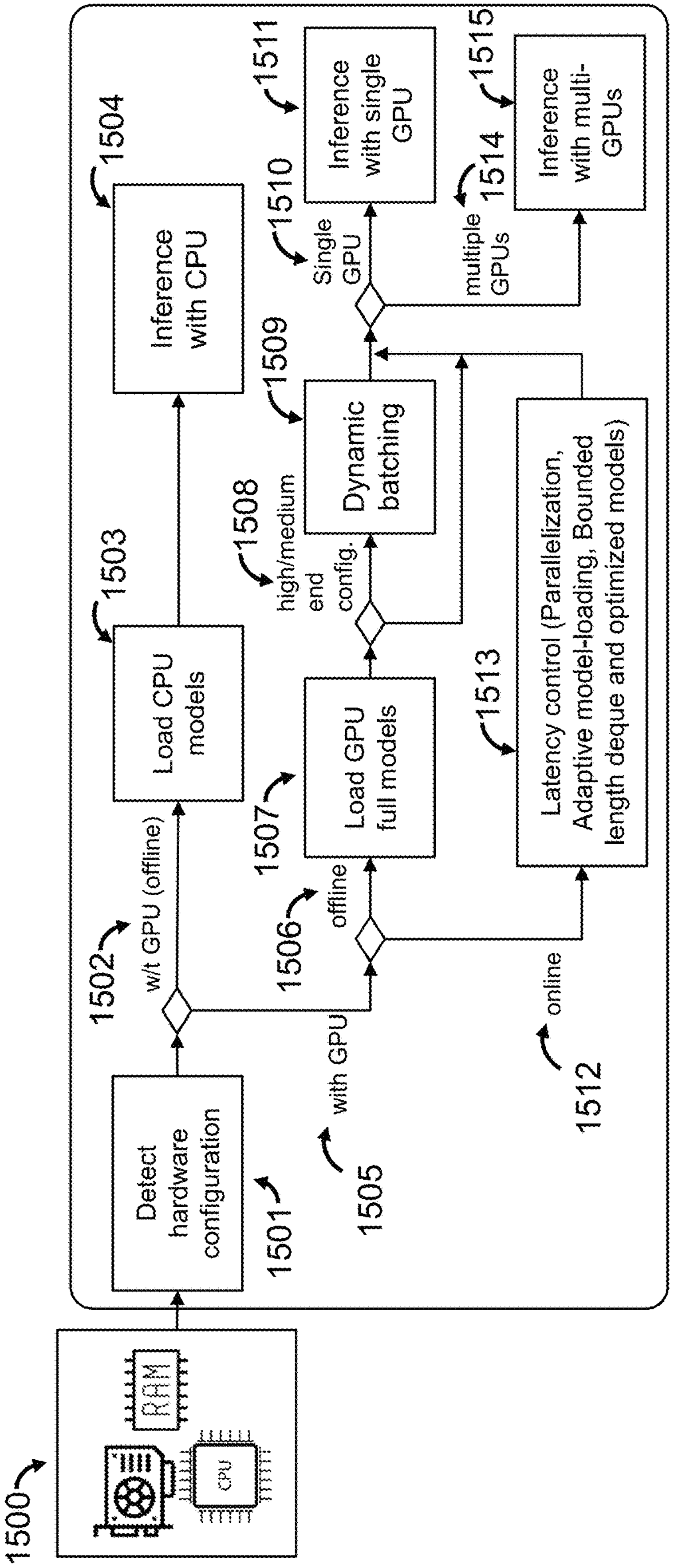
FIG. 15 illustrates how the computer-aided gastroscopy system can detect the available hardware configuration and make full use of its computation capability according to one embodiment of the present disclosure.

FIG. 15 illustrates how the computer-aided gastroscopy system can detect the available hardware configuration and make full use of its computation capability. In one embodiment, it performs configuration-aware optimization as follows: When this system is running, it first executes step 1501 to read the hardware configuration of the computer-aided gastroscopy system hardware platform 1500. If the hardware platform 1500 does not have a coprocessor such as a GPU card, then the system has to be run in off-line mode. Hence the path 1502 is taken. The system will load all the full neural models to the computer at step 1503 and start using the main CPU power to do inferencing at 1504.

If the hardware platform contains one or more coprocessors or GPU cards, the path 1505 is taken and the user can choose to run the system in either off-line mode or on-line mode. For off-line processing, path 1506 is chosen. The system then loads the full neural models to the coprocessors in preparation of the subsequent inferencing process. At this point, the system checks the hardware configuration and capability of each of the GPU cards at step 1508. If a GPU card has a medium to high-end configuration in terms of its memory size and processing speed, the system will execute the dynamic batching inference procedure at step 1509. Otherwise, it will skip this step. The details of the dynamic batching inference will be discussed later. At this juncture, the system further checks if the hardware platform 1500 has a single GPU or multiple GPUs. If it is the former, then the path 1510 is taken and the system performs all the neural inferencing using the single GPU at step 1511. If the system has multiple GPUs, then path 1514 is taken and it invokes another inferencing procedure with multiple GPU at step 1515.

If the system is selected to run in on-line mode, then path 1512 is taken and the system will execute the latency control step 1513. This step mainly tries to manage the response latency to an acceptable level so that users need not wait for a long time before getting the results. The details of this step will be discussed later. Also in this step, the optimized neural models are loaded to the GPU instead of the full neural models as the optimized neural models are optimized to run faster. After this step, the system will join the path to check if the hardware platform 1500 has a single GPU or multiple GPUs and proceed accordingly as mentioned before.

Figure 16:
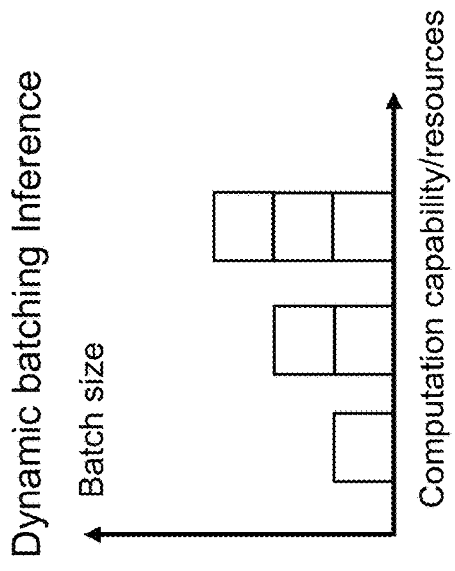
FIG. 16 shows the dynamic batching inference process according to one embodiment of the present disclosure.

As mentioned above, the system performs dynamic batching when it is to run in off-line mode and one or more GPU has sufficient resources. In dynamic batching, the system changes the batch size dynamically based on the computational power and memory availability of the GPU card. For example, when the GPU memory is sufficiently large, loading more images in a batch can speed up inferencing. FIG. 16 illustrates the relationship between the batch size vs. the GPU computation capability and resources available.

Figure 17:
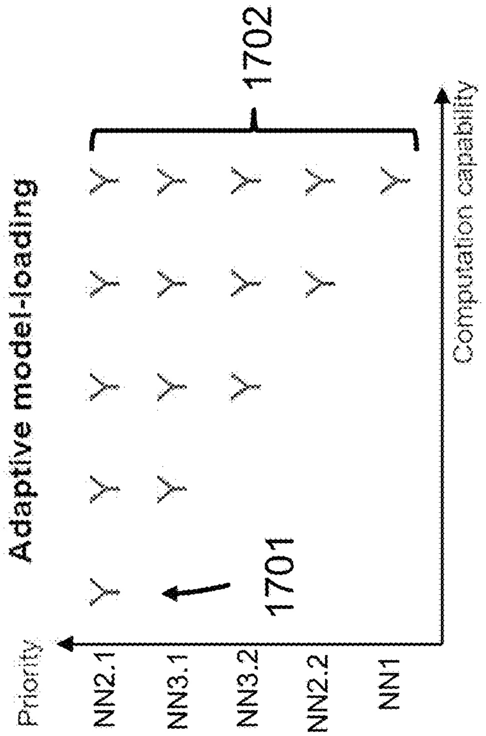
FIG. 17 shows the neural model priority arrangement according to one embodiment of the present disclosure.

When the system runs in on-line mode, it needs to optimize the response time. In one embodiment, the system exercises latency control. The system explores every opportunity of parallel processing to execute tasks like unified preprocessing and/or neural inferencing in parallel. Notice that in this case, the optimized neural models are loaded to the GPU as they can execute faster than the respective full models. In order to do that, the different neural models are prioritized according to their computational capacity requirements. FIG. 17 illustrates this priority arrangement which is based on the task importance in this application. In this Figure, the horizontal axis denotes the computation capability of a GPU and the vertical axis represents various neural models according to priority. As shown in this figure, NN1 is the least important task and hence it has the lowest priority, whereas NN2.1 is the most important task and is assigned the highest priority. Hence at any given time, the system makes use of this table to perform adaptive model loading. If the computation capability of the GPU is low, then only the NN2.1 model is loaded as shown in 1701. On the other hand, when computation capability is abundant, all five neural models can be loaded to the CPU as shown in reference label 1702. When more than one GPU is available, then the system will load some neural models to one GPU and the rest to the others so as to balance the workloads in order to achieve maximum reduction of inference time.

Figure 18:
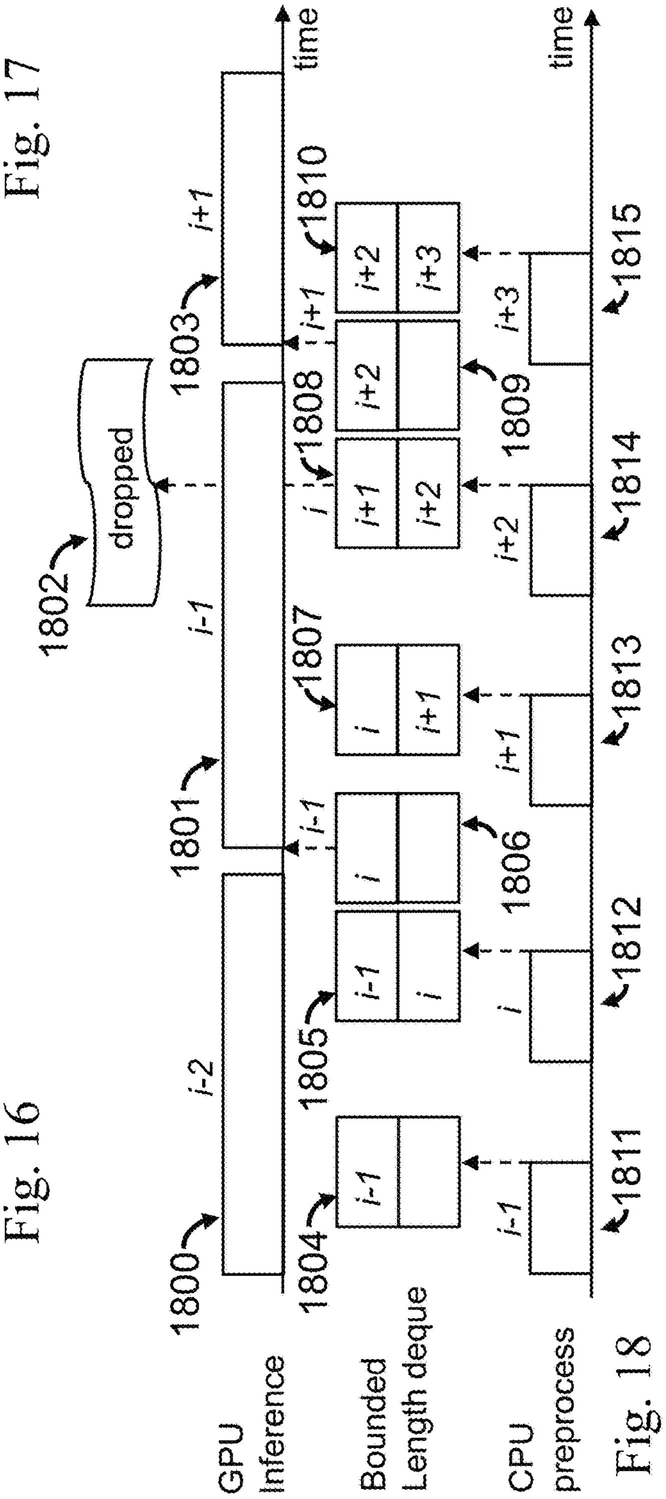
FIG. 18 illustrates the timing diagram of bounded length deque operation according to one embodiment of the present disclosure.

In another embodiment, the system assigns a bounded length task queue to each GPU and fills in tasks to this queue. FIG. 18 illustrates the timing diagram of bounded length deque operation in one exemplary embodiment. Refer now to FIG. 18. The horizontal axis refers to a timeline. The system's main CPU starts issuing tasks to a GPU. At the (i−1)th time slot, the main CPU issues a task as shown at time step 1811. At this point, the bounded queue is empty hence this task is placed at the highest slot of the queue as shown at reference label 1804 and is ready to enter to the GPU for execution. However, the GPU is still busy performing inferencing for a task entered at the $(i-2)^{th}$ time slot as shown at reference label 1800, so this task needs to wait. At the $i^{th}$ time slot, the CPU issues another task as shown at time step 1812 and this task also is put to the bounded queue. In this example, the size of the bounded queue has two slots, so the bounded queue is full as shown at reference label 1805. Sometime afterward, the GPU has finished executing the task entered at the $(i-2)^{th}$ time slot as shown at reference label 1800; hence the $(i-1)^{th}$ task at reference label 1805 is popped from the bounded queue and put to the GPU for execution as shown at reference label 1801. Afterward, the bounded queue has one entry which is the task entered at the $i^{th}$ time slot as shown at reference label 1806. At the $(i+1)^{th}$ time slot 1813, the main CPU issues a new task and it enters the bounded queue as shown at reference label 1807. At the (i+2)$^{th}$ time slot 1814, the main CPU again issues another task. However, the bounded queue is full, but GPU is still inferencing on the (i−1)$^{th}$ task as shown at reference label 1801. At this point, the system needs to drop the i$^{th}$ task from the bounded queue as shown at reference label 1802. Thereafter the bounded queue is now occupied with tasks entered at the (i+1)$^{th}$ time slot and the (i+2)$^{th}$ time slot as shown at reference label 1808. Right after this, the GPU has finished inferencing the (i−1)$^{th}$ task as shown at reference label 1801. Hence the (i+1)$^{th}$ task is popped from the bounded queue and entered into the GPU for inferencing as shown at reference label 1803. At this point, the bounded queue has only one entry as shown in reference label 1809. At the (i+3)$^{th}$ time slot, the CPU issues another task as shown at time slot 1815. This task enters the bounded queue 1810; and the process repeats itself.

This timing diagram illustrates that when the bounded queue is full and the GPU is still busy inferencing a previous task, a new task request to enter the bounded queue will cause the topmost task in the queue to be dropped. This may cause undesirable large latency and hence this scheme is only used in off-line mode but not in on-line mode.

With the priority arrangement as shown in FIG. 17 and the implementation of the bounded queue scheme illustrated in FIG. 18 as well as other latency control methods such as parallel computing, the system is able to make use of all the GPU hardware resources at run time to perform inferencing in parallel so as to minimize the latency time. The following table shows the performance improvement of the latency control scheme mentioned above.

TABLE 5

Performance improvement of the latency control scheme.

| Hardware config. | Optimized latency (ms) [mean/max] | Improvement [mean/max] |
|---|---|---|
| Dual NVIDIA ® GeForce RTX ™ 3090 24 GB | 23/35 | 30.3%/30% |
| Dual NVIDIA ® GeForce GTX ™ 1080Ti 8 GB | 39/57 | 26.4%/38.0% |
| One NVIDIA ® GeForce RTX ™ 2080 8 GB | 42/63 | 30%/41.7% |
| One NVIDIA ® GeForce GTX ™ 1060 6 GB | 73/95 | 45.9%/49.2% |

This table summarizes the experiments conducted on various GPU hardware cards with different memory resources. The improvement is measured against a target overall latency value of less than 120 msec. This value is specified by the end user. The second column shows the optimized latency in terms of mean and max values using the latency control scheme mentioned above; and the third column shows the percentage improvement. As observed from this table, the improvement ranges from slightly over 30% to up to 49%.

Figure 19:
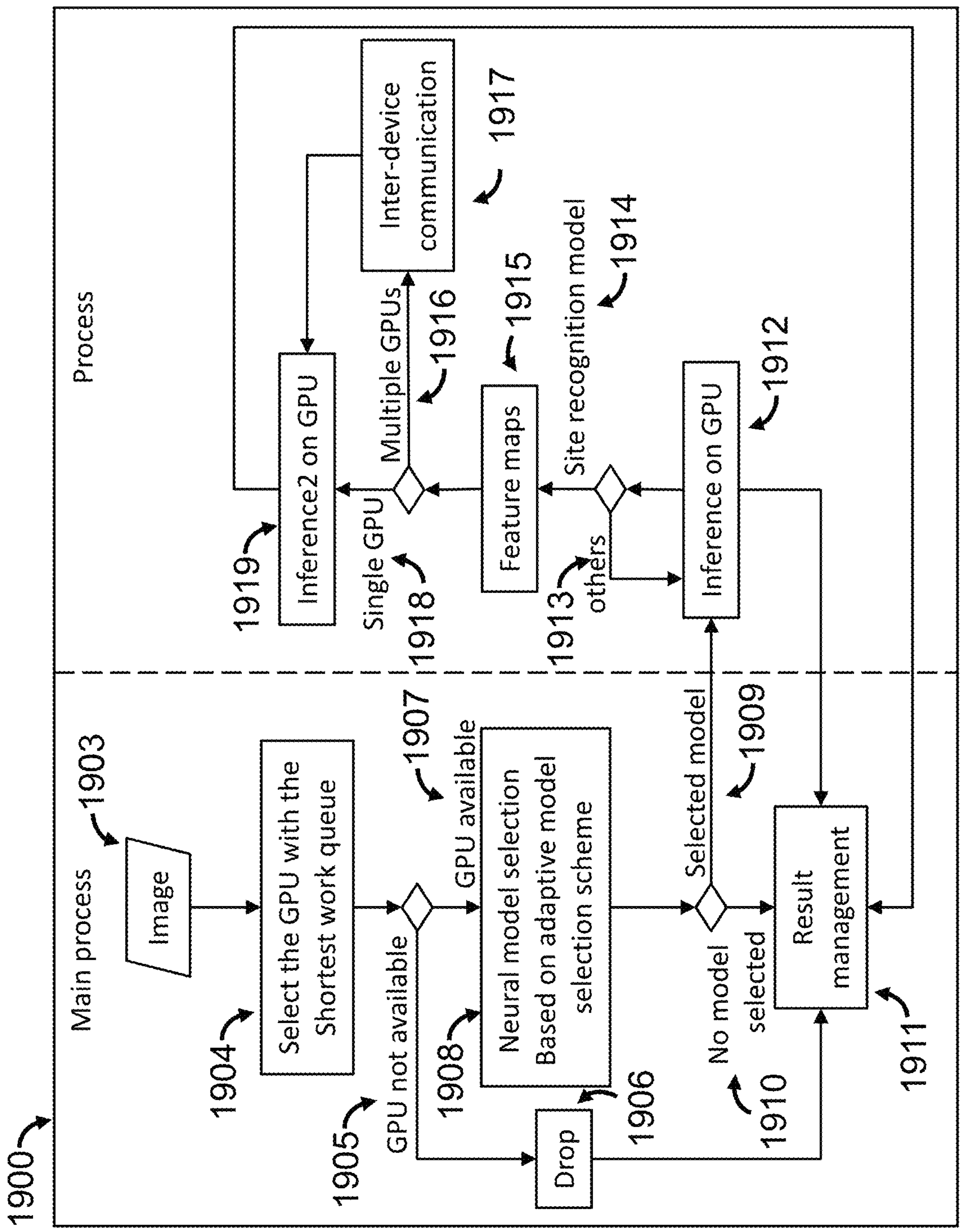
FIG. 19 shows the neural inferencing execution flow under on-line mode of operation according to one embodiment of the present disclosure.

FIG. 15 demonstrates how the computer-aided gastroscopy system configures the hardware resources in preparation of subsequent inferencing in on-line mode. When a gastric image is presented, the system will then execute the various inferencing tasks according to this configuration. FIG. 19 shows the actual execution flow of inferencing under on-line mode of operation.

Referring to FIG. 19, the main inferencing flow 1900 starts when a gastric image 1903 is received. The system first selects a GPU that has the shortest work queue at step 1904. If no GPU is available, then it will take the path of 1905 and drop the image at step 1906. It will then go to the result management 1911. If there is a GPU available, then the path 1907 is taken. One or more neural models are then selected using the adaptive model selection scheme mentioned in the previous paragraphs at step 1908. In case no neural model is selected for inferencing, the path 1910 is taken to go to the result management step 1911.

If a neural model is selected, the path 1909 is taken and a GPU will take up this neural model to start inferencing. If the selected neural model is not a site recognition neural model, then the path 1913 is taken and the GPU will continue its inferencing tasks at step 1912. The results are sent to the result management 1911. Otherwise, the path 1914 is taken and the site feature map of this image is extracted in step 1915. This process is computationally intensive. If the system has a single GPU, the path 1918 is taken to start inferencing at the step 1919 using this GPU. Otherwise, the path 1916 is taken. Since there is more than one GPU available, the whole task of site recognition is partitioned into subtasks and each GPU is to work on a subtask in parallel. Each subtask will produce intermediate results that need to be shared with other GPUs. Hence in step 1917, inter-device communication among GPUs is needed. Whether the system has a single or multiple GPU, the inference results are sent to the result management 1911.

FIG. 20 shows how the model selection is done in one exemplary embodiment. In this embodiment, there are two GPUs, namely GPU-0 and GPU-1. Each GPU is capable of executing neural models NN1, NN2.1, NN2.2, NN3.1 and NN3.2. However, depending on the available computation resources in GPU-0 and GPU-1 at the time of model selection, these neural models are assigned to the two GPUs differently. In this figure, the shaded area denotes that the GPU has a high level of computational resources available for neural model inferencing while the white area denotes that the GPU is quite occupied. According to the adaptive model loading table as shown in FIG. 17, NN2.1 is the highest priority task, followed by NN3.1, and NN1 is the lowest priority task. Hence in row 2001 of FIG. 20, both GPUs have low computational resources available for selection. In this exemplary case, NN2.1 and NN3.1, the first two highest priority tasks, are assigned to GPU-0 for execution while NN1, NN2.2 and NN3.2 are sent to GPU-1.

In row 2002, GPU-1 has higher computational resources available for selection. In this case, GPU-0 takes on NN1 and NN3.2 while GPU-1 takes on NN2.1, NN2.2 and NN3.1. Likewise, row 3. is the opposite of row 2 in terms of GPU resource availability. Hence in this case, GPU-0 takes on NN2.1, NN2.2 and NN3.1 while GPU-1 takes on NN1 and NN3.2.

As for row 2004 of FIG. 20, there are plenty of computational resources available for both GPUs and these tasks can be arbitrarily assigned to either GPU. In this exemplary case, GPU-0 takes on NN1, NN2.1 and NN2.2 while GPU-1 takes on NN3.1 and NN3.2.

The following table shows the inference speed comparison (in frames per second) between two systems. In this experiment, the CPU is an Intel Core i7-7800x running at a 3.5 GHz clock rate; and the GPU card is a dual GPU GeForce GTX 1080Ti. The experiment was to compare the inference speed, in terms of frames per second (FPS), to process a gastric video, when one of the GPUs is used (sing process case) vs both GPUs are used (multi-process case). This table shows that for a multi-process system, it can process 51 frames per second of video images as compared to only 19 frames for a single process system.

TABLE6

| Comparison of Inference speed between Single process and Multi-process | |
|---|---|
| | Inference speed (FPS) |
| Single process | 19 |
| Multi-process | 51 |

The system and method of the present invention may be implemented in the form of a software application running on a computerized system. Further, portions of the methods may be executed on one such computerized system, while the other portions are executed on one or more other such computerized systems. Examples of the computerized system include a mainframe, personal computer, handheld computer, server, etc. The software application may be stored on a recording media locally accessible by the computer system and accessible via a hard-wired or wireless connection to a network, for example, a local area network or the Internet.

The computerized system may include, for example, a processor, random access memory (RAM), a printer interface, a display unit, a local area network (LAN) data transmission controller, a LAN interface, a network controller, an internal bus, and one or more input devices, for example, a keyboard, mouse, etc. The computerized system can be connected to a data storage device.

Figure 21:
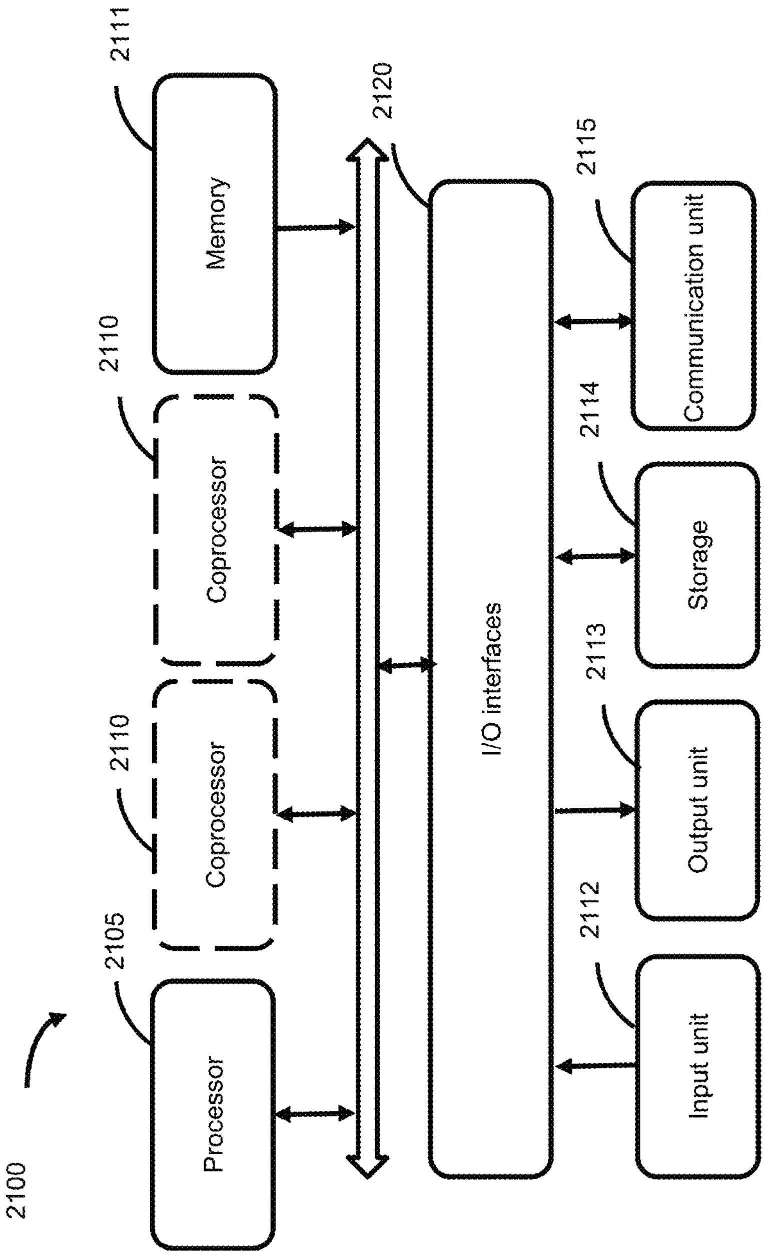
FIG. 21 shows hardware schematic diagram of a computer-aided gastroscopy system in one exemplary embodiment of the present disclosure.

FIG. 21 is a schematic diagram of a computerized system 2100 for a multifunctional computer-aided gastroscopy system according to an embodiment of the present invention, consisting of both the hardware and software components that can be used to implement the embodiments of the present invention.

The hardware components in the present embodiment further comprise the processor 2105, memory 2111 and multiple interfaces. It may optionally comprise one or more coprocessor 2110 to speed up the computation. A plurality of components in the computerized system 2100 is connected to the I/O interface 2120, including input unit 2112, output unit 2113, storage unit 2114 and communication unit 2115, which include, but not limited to, network card, modem, radio communication transceiver, etc. In another embodiment, the present disclosure may also be deployed in a distributed computing environment that includes more than one computerized system 2100 connected together through one or more network interfaces in the communication unit 2115. The network interface can include one or more of the internet, an intranet, an extranet, a cellular network, a local area network (LAN), a home area network (HAN), a metropolitan area network (MAN), a wide area network (WAN), a Bluetooth network, public and private networks, etc.

The processor 2105 can be a central processing unit (CPU), microprocessor, microcontrollers, digital signal processor (DSP), field-programmable gate arrays (FPGA), application-specific integrated circuits (ASIC), etc., for controlling the overall operation of memory (such as random access memory (RAM) for temporary data storage, and/or read-only memory (ROM) for permanent data storage, and firmware). One or more processors can communicate with each other and memory and perform operations and tasks that implement one or more blocks of the flow diagrams discussed herein.

Similarly, the coprocessor 2110 may be a Graphics Processing Unit (GPU) card which comprises its own processing unit, and random-access memory (RAM); or it may be other hardware circuitries that accelerate mathematic calculations such as a digital signal processor (DSP), field-programmable gate arrays (FPGA), application-specific integrated circuits (ASIC), etc. One or more coprocessors 2110 can communicate with the processor 2105 and access the memory 2111. They can also communicate with each other and memory 2111 and perform operations and tasks that implement one or more blocks of the flow diagrams discussed herein.

The memory 2111, for example, stores applications, data, programs, algorithms (including software to implement or assist in implementing example embodiments) and other data. Memory 2111 can include dynamic or static random-access memory (DRAM or SRAM) or read-only memory such as Erasable and Programmable Read-Only Memories (EPROMs), Electrically Erasable and Programmable Read-Only Memories (EEPROMs) and flash memories, as well as other memory technologies, singly or jointly combined.

The storage 2114 typically includes persistence storage such as magnetic disks such as fixed and removable disks; other magnetic media including tape; optical media such as Compact Disks (CDs) or Digital Versatile Disks (DVDs), and semiconductor storage devices such as flash memory cards, solid-state drive, EPROMs, EEPROMS or other storage technologies, singly or in combination. Note that the instructions of the software discussed above can be provided on computer-readable or machine-readable storage medium, or alternatively, can be provided on multiple computer-readable or machine-readable storage media distributed in a large system having possibly plural nodes. Such computer-readable or machine-readable medium or media is (are) considered to be part of an article (or article of manufacture). An article or article of manufacture can refer to any manufactured single component or multiple components.

The input unit 2112 is the interfacing component that connects the computerized system 2100 to data input devices such as keyboard, keypad, pen-based device, mouse or other point devices, voice-input apparatus, scanner, or other input technologies. According to an embodiment of the present invention, the input unit 1812 may include a gastroscopy instrument that comprises an image camera which can be inserted inside the gastrointestinal track. The output unit 2113 is the interfacing component for the computerized system 2100 to send data to the output devices such as a CRT or flat panel display monitor, printer, voice output apparatus, laud speaker or other output technologies. The communication unit 2115 may typically include the serial or parallel interface and the USB (Universal Serial Bus) interfaces, and other interfacing technologies. The communication unit 2115 may also enable the computerized system 2100 to exchange information with external data-processing devices via a data communication network such as the Personal Area Network (PAN), the Local Area Network (LAN), the Wide Area Network (WAN), the Internet, and other data communication network architectures. The communication unit 2115 can include the Ethernet interface, the Wireless LAN interface device, the Bluetooth interfacing device and other networking devices, singly or in combination.

The processor 2105 is capable of executing software program instructions stored in the memory 2111. The software program further includes the operating system, and the application software such as the endoscopic image analysis module. The operating system is to manage all the hardware resources, and schedule executing priorities for all tasks and processes.

Blocks and/or methods discussed herein can be executed and/or made by a user, a user agent (including machine learning agents and intelligent user agents), a software application, an electronic device, a computer, firmware, hardware, a process, a computer system, and/or an intelligent personal assistant. Furthermore, blocks and/or methods discussed herein can be executed automatically with or without instruction from a user.

It should be understood for those skilled in the art that the division between hardware and software is a conceptual division for ease of understanding and is somewhat arbitrary. Moreover, it will be appreciated that peripheral devices in one computer installation may be integrated into the host computer in another. Furthermore, the application software systems may be executed in a distributed computing environment. The software program and its related databases can be stored in a separate file server or database server and are transferred to the local host for execution. The computerized system 2100 as shown in FIG. 21 is therefore an exemplary embodiment of how the present invention can be implemented. Those skilled in the art will appreciate that alternative embodiments can be adapted to implement the present invention.

The exemplary embodiments of the present invention are thus fully described. Although the description referred to particular embodiments, it will be clear to one skilled in the art that the present invention may be practiced with the variation of these specific details. Hence this invention should not be construed as limited to the embodiments set forth herein.

Methods discussed within different figures can be added to or exchanged with methods in other figures. Further, specific numerical data values (such as specific quantities, numbers, categories, etc.) or other specific information should be interpreted as illustrative for discussing example embodiments. Such specific information is not provided to limit example embodiment.

What is claimed is:

1. A computer-aided gastroscopy system, comprising:

a central processor unit coupled with a memory that stores an executable software program, wherein the software program comprises:

an AI image processing system that analyzes a gastric image sequence obtained from a gastroscopy instrument, wherein the AI image processing system comprises at least three modules at the architecture level that cooperatively perform image quality assessment; lesion detection; cancer identification; HP classification; and site recognition, wherein at least one of the modules comprises one or more neural models, the neural model extracting different but related information from the gastric image sequence and sharing the information extracted from the gastric image sequence with other modules; and at least one said neural model fuses HP infection features and site information extracted from other neural models together to boost the classification accuracy of the computer-aided gastroscopy system.

2. The system according to claim 1, wherein the at least three modules comprise:

a first module for image quality control to filter out unqualified images in the gastric image sequence;

a second module for lesion detection, cancer identification and lesion tracking; and a third module for classifying HP infection and site recognition, wherein each of these modules comprises one or more neural models.

3. The system according to claim 2, wherein the third module further comprises a composite neural model comprising:

a first neural model taking the gastric image sequence as input, performing HP feature extraction, and outputting a first number of feature channels;

a second neural model also taking the gastric image sequence as input, performing site feature extraction comprising the spatial and temporal site information of the gastrointestinal track, and outputting a second number of feature channels; and a third neural model taking the concatenation of the first number of feature channels and the second number of feature channels as input and producing a third number of class labels, each of the class labels indicating a HP infection feature.

4. The system of claim 3, wherein the first neural model products a first tensor of sixty-four channel elements; the second neural model products a second tensor of twelve channel elements, each of the twelve channel elements corresponding to a site classification label; and the third neural model takes the concatenation of the first tensor and the second tensor as input and outputs nine element classification labels corresponding to nine of the HP infection features.

5. The system according to claim 3, further comprising a unified preprocessing module wherein the unified preprocessing module takes the gastric image sequence as input and produces a unified tensor as output for each image in the gastric image sequence, the unified tensor is fed to the neural models of the first module, the second module and the third module of the AI image processing system.

6. The system according to claim 5, wherein neural network architectures of the first module, the second module and the third module are adjusted such that output tensors of the neural model remain the same as if each of the neural network architectures uses a distinct preprocessing module specially designed for the neural network architecture.

7. The system according to claim 5, wherein neural network architectures of the first module, the second module and the third module are adjusted so that the performance of each neural model does not degrade.

8. The system according to claim 5, wherein if either the height or the width of the image in the gastric image sequence entering into the unified preprocessing module is higher than a threshold, a parallelized resizing process is invoked to resize the image wherein the parallelized resizing process comprises the following steps:

padding the original image with a row of zeros if the height is an odd number and with a column of zeros if the width is an odd number;

partitioning a padded image into four quadrants;

resizing each of the quadrants in parallel to produce four resized quadrants; and stitching the four resized quadrants together to obtain a uniform resized image.

9. The system according to claim 2, wherein the neural model of the first module is trained using an image quality dataset to produce a full image quality neural model;

the one or more neural models of the second module is trained using a lesion dataset to produce a full lesion detection neural model; and the one or more neural models of the third module is trained using a gastric site dataset and a *H. pylori* dataset to produce a full HP-plus-site neural model.

10. The system according to claim 9, further comprising a model pruning and quantization module wherein the full image quality neural model, the full lesion detection neural model and the full HP-plus-site neural model are optimized by pruning the layer connections and quantizing the connection weights to produce an optimized image quality neural model; an optimized lesion detection neural model and an optimized HP-plus-site neural model respectively.

11. The system according to claim 10, wherein the computer-aided gastroscopy system further comprises at least one coprocessor and the software program executed at the central processor unit judiciously allocates subtasks initiated by each of the modules to the at least one coprocessor depending on a pre-assigned priority of the subtasks and the capability of each of the coprocessor such that the computer-aided gastroscopy system is able to achieve high detection and classification accuracy with low latency response to a user.

12. The system according to claim 11, wherein when the computer-aided gastroscopy system is equipped with the at least one coprocessor, the computer-aided gastroscopy system is capable of operating in both off-line processing mode and on-line processing mode.

13. The system according to claim 12, wherein when the computer-aided gastroscopy system is set to operate in the off-line processing mode, the computer-aided gastroscopy system configures each of the at least one coprocessor to operate a dynamic batching process which comprises the steps of:

loading at least one full neural model to the coprocessor; and loading a batch of gastric images to the coprocessor wherein the batch size is dynamically determined based on the computation capability and resources available in the coprocessor.

14. The system according to claim 12, wherein when the computer-aided gastroscopy system is equipped with the at least one coprocessor and is set to operate in the on-line processing mode, the computer-aided gastroscopy system performs a latency control procedure which comprises the steps of:

pre-determining the loading priority of each of the optimized neural models according to its computational resource requirements;

loading one or more of the optimized neural models to each of the coprocessor according to the loading priority and the hardware configuration of the coprocessor;

establishing a fixed length task queue to each of the coprocessor for the central processing unit to issue subtasks to the task queue for the coprocessor to execute; and enabling each of the at least one coprocessor to operate in parallel wherein whenever the coprocessor becomes idle, the coprocessor deques the subtask from the task queue associated with this coprocessor and starts executing the subtask whenever the coprocessor becomes idle.

15. The system according to claim 14, wherein when the computer-aided gastroscopy system obtains the gastric images, the computer-aided gastroscopy system performs a resource-aware inferencing procedure which comprises the steps of:

selecting a coprocessor with the shortest work queue among the at least one coprocessor as a designated coprocessor;

loading one or more of the optimized neural model to the designated coprocessor based on a neural model priority and the resource availability at the designated coprocessor;

repeating the selecting and loading steps such that as many of the optimized neural models are loaded to one or more of the coprocessor as possible;

enabling each of the neural models to start inferencing at each of the at least one coprocessor in parallel;

performing inter-coprocessor communication among the coprocessors when an inferencing task of the neural model is split to run on more than one of the coprocessors and an intermediate result generated by one of the coprocessors needs to be shared to the other coprocessors; and collecting the inferencing results of each of the neural models and reporting back to the computer-aided gastroscopy system.

16. A method of processing a gastric image sequence by a computer-aided gastroscopy system, comprising:

obtaining the gastric image sequence from a gastroscopy instrument;

analyzing the gastric image sequence by an AI image processing system comprising at least three modules at the architecture level that cooperatively perform image quality assessment; lesion detection, cancer identification, HP classification and lesion site recognition, wherein at least one of the modules comprises one or more neural models, the neural model extracting different but related information from the gastroscopy image sequence and sharing the information extracted from the gastroscopy image sequence with other modules; and at least one said neural model fuses the HP infection features and site information extracted from other neural network models together to boost the classification accuracy of the computer-aided gastroscopy system;

creating a list of subtasks by each of the at least three modules to be executed by the computer-aided gastroscopy system; and reducing the latency response to a user when the computer-aided gastroscopy system further comprises at least one coprocessor and the software program executed at the central processor unit of the computer-aided gastroscopy system judiciously allocates subtasks to the at least one coprocessor depending on a pre-assigned priority of the subtasks and the capacity and capability of each of the coprocessor such that the computer-aided gastroscopy system is able to achieve high detection and classification accuracy with low latency response to the user.

17. The method of claim 16, wherein the analyzing step further comprises the steps of:

filtering out unqualified images in the gastric image sequence by the neural model in a first module;

performing lesion detection, cancer identification and lesion tracking by at least one of the neural models in a second module; and classifying HP infection and recognizing gastrointestinal site by at least one of the neural models in a third module.

18. The method of claim 17, wherein the classifying and recognizing step further comprises the steps of:

outputting a first number of feature channels by a first neural model which takes the gastric image sequence as input and performs HP feature extraction;

outputting a second number of feature channels by a second neural model which also takes the gastric image sequence as input and performs site feature extraction comprising spatial and temporal site information of the gastrointestinal track; and producing a third number of class labels by a third neural model which takes the concatenation of the first number of feature channels and the second number of feature channels as input, wherein each of the class labels indicating a HP infection feature.

19. The method of claim 18, wherein the second neural model is a composited neural model comprising a site feature extractor model, a LSTM model and a final neural model and the composited neural model is trained according to the following steps:

creating a cumulative batch of gastric images from a full set of labelled gastric images stored in a gastric site dataset;

training an auxiliary neural network using the cumulative batch of gastric images;

copying the entire auxiliary neural network and using the entire auxiliary neural network as a feature extractor of the composited neural model wherein the connection weights of the feature extractor will not be modified during the subsequent training process;

creating a pseudo video using the full set of labelled gastric images and collecting a predefined number of labelled gastric images from the pseudo video to form a batch unit;

grouping a predefined number of batch units together as a batch group and sending the batch group to the feature extractor to produce a feature tensor of the batch group;

feeding the feature tensor to the LSTM model which produces an intermediate tensor;

sending the intermediate tensor to the final neural model comprising at least one fully connected layer wherein the output tensor of the final neural model comprises a site vector, each element in the site vector is a site label and represents a gastric site location and the site vector becomes the feature channels of the second neural model.

20. The method of claim 19, wherein the pseudo video is created according to the following steps:

sorting the labelled gastric images in the gastric dataset in ascending order according to the index of the site label to obtain a sorted list of gastric images creating a pre-specified number of random generators, each of the random generators generating random numbers within a predetermined random range;

selecting one of the random generators to generate an initial random number and using that initial random number to select a gastric image from the sorted list as an anchored image;

collecting a set of random numbers from each of the plurality of random generators wherein the total number of random numbers collected is a predefined number being the batch size of the batch unit;

converting the set of random numbers into an index list offset by the index of the anchored image; and using the offset index list to select gastric images from the sorted list to form the batch unit.

* * * * *